United States Patent
Al-Jilaihawi et al.

(10) Patent No.: US 10,869,681 B2
(45) Date of Patent: Dec. 22, 2020

(54) DEVICE TO PERCUTANEOUSLY TREAT HEART VALVE EMBOLIZATION

(71) Applicant: Cedars-Sinai Medical Center, Los Angeles, CA (US)

(72) Inventors: Hasanian Al-Jilaihawi, West Hollywood, CA (US); Rajendra Makkar, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 310 days.

(21) Appl. No.: 15/025,014

(22) PCT Filed: Oct. 16, 2014

(86) PCT No.: PCT/US2014/060966
§ 371 (c)(1),
(2) Date: Mar. 25, 2016

(87) PCT Pub. No.: WO2015/058001
PCT Pub. Date: Apr. 23, 2015

(65) Prior Publication Data
US 2016/0235422 A1    Aug. 18, 2016

Related U.S. Application Data

(60) Provisional application No. 61/892,381, filed on Oct. 17, 2013.

(51) Int. Cl.
*A61B 17/221* (2006.01)
*A61B 17/50* (2006.01)
(Continued)

(52) U.S. Cl.
CPC ...... *A61B 17/221* (2013.01); *A61B 17/00234* (2013.01); *A61B 17/50* (2013.01);
(Continued)

(58) Field of Classification Search
CPC .................. A61F 2/2427; A61F 2/2436; A61F 2002/9528; A61F 2002/9534; A61F 2/01;
(Continued)

(56) References Cited

U.S. PATENT DOCUMENTS

| | | | |
|---|---|---|---|
| 4,694,838 A | 9/1987 | Wijayarthna et al. | |
| 4,738,667 A | 4/1988 | Galloway | |

(Continued)

FOREIGN PATENT DOCUMENTS

| | | |
|---|---|---|
| CN | 1106647 A | 8/1995 |
| CN | 1647777 A | 8/2005 |

(Continued)

OTHER PUBLICATIONS

Crushing. (n.d.) American Heritage Dictionary of the English Language, Fifth edition. (2011). Retrieved Oct. 1 208 from https://www.thefreedictionary.com/crushing (Year: 2011).*

(Continued)

*Primary Examiner* — Kathleen S Holwerda
*Assistant Examiner* — Kankindi Rwego
(74) *Attorney, Agent, or Firm* — Nixon Peabody LLP

(57) ABSTRACT

The present invention provides devices and methods for percutaneously retrieving an embolized or malpositioned heart valve or foreign bodies from a patient's body. Several of these devices may include a catheter system with expandable and retractable baskets attached to a catheter and guidewire system. The guidewire may be inserted through the lumen of the embolized or malpositioned heart valve, capturing the valve in the baskets, and deploying a mechanism to crush the valve within the baskets. Then the crushed baskets and valve may be retrieved either from the body or to a safer location such as but not limited to the descending (Continued)

aorta. This system is advantageous because it does not require open surgery to retrieve the valve or embolized material.

26 Claims, 17 Drawing Sheets

(51) Int. Cl.
  *A61B 17/00* (2006.01)
  *A61B 17/22* (2006.01)
  *A61F 2/24* (2006.01)

(52) U.S. Cl.
  CPC .............. *A61B 2017/00243* (2013.01); *A61B 2017/00477* (2013.01); *A61B 2017/22035* (2013.01); *A61B 2017/22038* (2013.01); *A61B 2017/22097* (2013.01); *A61F 2/2427* (2013.01)

(58) Field of Classification Search
  CPC .... A61F 2/013; A61F 2002/016; A61B 17/50; A61B 17/221; A61B 2017/00234; A61B 2017/00243; A61B 2017/00477; A61B 2017/22035; A61B 2017/22038; A61B 2018/00214; A61B 2018/0267; A61B 1/00085; A61B 5/6858
  See application file for complete search history.

(56) References Cited

U.S. PATENT DOCUMENTS

| | | |
|---|---|---|
| 5,423,829 A | 6/1995 | Pham et al. |
| 5,833,632 A | 11/1998 | Jacobsen et al. |
| 5,964,744 A | 10/1999 | Balbierz et al. |
| 5,964,797 A | 10/1999 | Ho |
| 5,972,019 A | 10/1999 | Engleson et al. |
| 6,059,779 A | 5/2000 | Mills |
| 6,086,557 A | 7/2000 | Morejohn et al. |
| 6,217,611 B1 | 4/2001 | Klostermeyer |
| 6,287,277 B1 | 9/2001 | Yan |
| 6,350,282 B1 | 2/2002 | Eberhardt |
| 6,425,909 B1 * | 7/2002 | Dieck ..................... A61F 2/013 606/200 |
| 6,589,230 B2 | 7/2003 | Gia et al. |
| 6,953,473 B2 | 10/2005 | Porter |
| 6,964,657 B2 | 11/2005 | Cragg et al. |
| 6,976,965 B2 | 12/2005 | Corl et al. |
| 7,134,994 B2 | 11/2006 | Alpert et al. |
| 7,340,288 B1 | 3/2008 | Karicherla et al. |
| 7,935,144 B2 | 5/2011 | Robin et al. |
| 8,070,800 B2 | 12/2011 | Lock et al. |
| 8,092,524 B2 | 1/2012 | Nugent et al. |
| 8,372,069 B2 | 2/2013 | Kassab |
| 8,377,112 B2 | 2/2013 | Griffin et al. |
| 3,430,927 A1 | 4/2013 | Bonhoeffer |
| 8,408,214 B2 | 4/2013 | Spenser |
| 8,491,648 B2 | 7/2013 | Hassan et al. |
| 2002/0169474 A1 | 11/2002 | Kusleika et al. |
| 2003/0236533 A1 | 12/2003 | Wilson et al. |
| 2004/0073141 A1 | 4/2004 | Hartley et al. |
| 2004/0172081 A1 | 9/2004 | Wang |
| 2005/0203425 A1 | 9/2005 | Langston |
| 2005/0240200 A1 | 10/2005 | Bergheim |
| 2005/0256566 A1 | 11/2005 | Gabbay |
| 2005/0267010 A1 | 12/2005 | Goodson et al. |
| 2006/0064114 A1 | 3/2006 | Obitsu et al. |
| 2006/0155305 A1 * | 7/2006 | Freudenthal ......... A61B 17/221 606/114 |
| 2006/0195137 A1 | 8/2006 | Sepetka et al. |
| 2006/0287719 A1 | 12/2006 | Rowe et al. |
| 2007/0050021 A1 | 3/2007 | Johnson |
| 2007/0203562 A1 | 8/2007 | Malewicz et al. |
| 2008/0027334 A1 | 1/2008 | Langston |
| 2008/0033467 A1 | 2/2008 | Miyamoto et al. |
| 2008/0183273 A1 | 7/2008 | Mesana et al. |
| 2008/0221551 A1 | 9/2008 | Goodson et al. |
| 2008/0306499 A1 | 12/2008 | Katoh et al. |
| 2008/0319541 A1 | 12/2008 | Filsoufi |
| 2009/0082678 A1 | 3/2009 | Smith |
| 2009/0248143 A1 | 10/2009 | Laham |
| 2009/0259292 A1 | 10/2009 | Bonhoeffer |
| 2009/0276040 A1 | 11/2009 | Rowe et al. |
| 2010/0030330 A1 | 2/2010 | Bobo et al. |
| 2010/0076549 A1 | 3/2010 | Keidar et al. |
| 2010/0094209 A1 | 4/2010 | Drasler et al. |
| 2010/0168840 A1 | 7/2010 | Kassab |
| 2010/0185275 A1 | 7/2010 | Richter et al. |
| 2010/0191272 A1 | 7/2010 | Keating |
| 2010/0211094 A1 | 8/2010 | Sargent |
| 2010/0331948 A1 | 12/2010 | Turovskiy et al. |
| 2011/0137397 A1 | 6/2011 | Chau et al. |
| 2012/0059458 A1 | 3/2012 | Buchbinder et al. |
| 2012/0130230 A1 | 5/2012 | Eichler et al. |
| 2012/0158129 A1 | 6/2012 | Duffy et al. |
| 2012/0283757 A1 | 11/2012 | Miller et al. |
| 2012/0283812 A1 | 11/2012 | Lagodzki et al. |
| 2012/0283820 A1 | 11/2012 | Tseng et al. |
| 2012/0310328 A1 | 12/2012 | Olson et al. |
| 2012/0310330 A1 | 12/2012 | Buchbinder et al. |
| 2013/0090726 A1 | 4/2013 | Rowe et al. |
| 2013/0109960 A1 | 5/2013 | Stinis |
| 2013/0116779 A1 | 5/2013 | Weber |
| 2013/0166017 A1 | 6/2013 | Cartledge et al. |
| 2013/0190857 A1 | 7/2013 | Mitra et al. |
| 2013/0190865 A1 | 7/2013 | Anderson |
| 2013/0261738 A1 | 10/2013 | Clague et al. |
| 2013/0261739 A1 | 10/2013 | Kuehn |
| 2013/0274618 A1 | 10/2013 | Hou et al. |
| 2013/0331864 A1 | 12/2013 | Jelich et al. |
| 2013/0331921 A1 | 12/2013 | Roubin |
| 2014/0114402 A1 | 4/2014 | Arlberg et al. |
| 2014/0135799 A1 | 5/2014 | Henderson |
| 2014/0171958 A1 * | 6/2014 | Baig ................ A61B 17/22032 606/108 |
| 2014/0194981 A1 | 7/2014 | Menk et al. |
| 2014/0200662 A1 | 7/2014 | Eftel et al. |
| 2014/0222144 A1 | 8/2014 | Eberhardt et al. |
| 2014/0236287 A1 | 8/2014 | Clague et al. |
| 2014/0243966 A1 | 8/2014 | Garde et al. |
| 2014/0277419 A1 | 9/2014 | Garde et al. |
| 2014/0303719 A1 | 10/2014 | Cox et al. |
| 2014/0350669 A1 | 11/2014 | Gillespie et al. |
| 2016/0206424 A1 | 7/2016 | Al-Jilaihawi et al. |
| 2016/0228013 A1 | 8/2016 | Al-Jilaihawi et al. |
| 2016/0228241 A1 | 8/2016 | Al-Jilaihawi et al. |
| 2016/0302920 A1 | 10/2016 | Al-Jilaihawi |
| 2016/0310699 A1 | 10/2016 | Al-Jilaihawi |
| 2018/0078363 A1 | 3/2018 | Al-Jilaihawi |

FOREIGN PATENT DOCUMENTS

| | | |
|---|---|---|
| CN | 101474102 A | 7/2009 |
| CN | 101489504 A | 7/2009 |
| CN | 101947146 A | 1/2011 |
| CN | 101972177 A | 2/2011 |
| CN | 103237523 A | 8/2013 |
| CN | 104220028 A | 12/2014 |
| CN | 104334119 A | 2/2015 |
| CN | 105611871 A | 5/2016 |
| CN | 105611889 A | 5/2016 |
| CN | 105744969 A | 7/2016 |
| CN | 105764447 A | 7/2016 |
| CN | 107405191 A | 11/2017 |
| EP | 2732796 A1 | 5/2014 |
| EP | 3054838 A1 | 8/2016 |
| EP | 3057522 A1 | 8/2016 |
| EP | 3079633 A1 | 10/2016 |
| EP | 3099345 A1 | 12/2016 |
| EP | 3267940 A1 | 1/2018 |
| WO | 1996017644 A1 | 6/1996 |
| WO | 1998048879 | 11/1998 |
| WO | 99/15223 A1 | 4/1999 |
| WO | 99/15227 A1 | 4/1999 |

(56) References Cited

FOREIGN PATENT DOCUMENTS

| | | | |
|---|---|---|---|
| WO | 1999015223 A1 | 4/1999 |
| WO | 0249511 A1 | 6/2002 |
| WO | 2005059379 A1 | 6/2005 |
| WO | 2007081820 A1 | 7/2007 |
| WO | 2010085659 A1 | 7/2010 |
| WO | 2011039091 A1 | 4/2011 |
| WO | 2012009675 A2 | 1/2012 |
| WO | 2012161769 A1 | 11/2012 |
| WO | 2012/173697 A1 | 12/2012 |
| WO | 2013061281 A1 | 5/2013 |
| WO | 2013072777 A2 | 5/2013 |
| WO | 2014145469 A1 | 9/2014 |
| WO | 2015/054296 A1 | 4/2015 |
| WO | 2015/057735 A1 | 4/2015 |
| WO | 2015/057995 A2 | 4/2015 |
| WO | 2015/058001 A1 | 4/2015 |
| WO | 2015/089334 A1 | 6/2015 |
| WO | 2015/117025 A1 | 8/2015 |
| WO | 2016145250 A1 | 9/2016 |

OTHER PUBLICATIONS

Compress. Merriam-Webster.com. Merriam-Webster, n.d. Web. Oct. 1, 2018 (Year: 2018).*
EP 15743048.9 Extended Search Report dated Aug. 24, 2017, 8 pages.
PCT/US2014/060966 International Preliminary Report on Patentability dated Apr. 28, 2016; 6 pages.
PCT/US2014/069849 International Preliminary Report on Patentability dated Jun. 14, 2016; 7 pages.
PCT/US2015/013956 International Preliminary Report on Patentability dated Aug. 2, 2016; 7 pages.
PCT/US2014/059547 International Preliminary Report on Patentability dated Apr. 12, 2016; 6 pages.
PCT/US2014/060526 International Search Report and Written Opinion dated Feb. 10, 2015; 7 pages.
PCT/US2014/060957 International Search Report and Written Opinion dated Apr. 1, 2015; 10 pages.
PCT/US2014/060966 International Search Report and Written Opinion dated Jan. 29, 2015; 6 pages.
PCT/US2014/059547 International Search Report and Written Opinion dated Mar. 3, 2015; 9 pages.
PCT/US2014/069849 International Search Report and Written Opinion dated Mar. 2, 2015; 8 pages.
PCT/US2015/013956 International Search Report and Written Opinion dated Jun. 26, 2015; 10 pages.
Astarci et al. Transapical explantation of an embolized transcatheter valve. Interact Cardiovasc Thorac Surg (2011). 13:1-2.
Blows et al. The pressure wire in practice. Heart (2007). 93:419-422.
Bonhoeffer et al. The multi-track angiography catheter: a new tool for complex catheterisation in congenital heart disease. Heart (1996). 76:173-177.
Chiam et al. Percutaneous Transcatheter Mitral Valve Repair. J Am Coll Cardiol (2011). 4(1):1-13.
Ho, S.Y. Structure and anatomy of the aortic root. Eur J Echocardiogr (2009). 10:i3-i10.
Jolicoeur et al. Tiara: A Novel Catheter-Based Mitral Valve Bioprosthesis Initial Experiments and Short-Term Pre-Clinical Results. J Am Coll Cardiol (2012). 60(15)1430-1431.
Lange et al. Diagnostic Cardiac Catheterization. Circulation (2003). 107:e111-e113.
Masson et al. Percutaneous Treatment of Mitral Regurgitation. Circ Cardiovasc Interv (2009). 2:140-146.
McCarthy et al. Anatomy of the mitral valve: understanding the mitral valve complex in mitral regurgitation. Eur J Echocardiogr (2010). 11:i3-i9.
Ormiston et al. Bioabsorbable Coronary Stents (2009). Circ Cardiovasc Interv (2009). 2:255-260.
Sievers et al. The everyday used nomenclature of the aortic root components: the tower of Babel? Eur J Cardio-Thorac Surg (2011). 0:1-5.
Sinning et al. Aortic Regurgitation Index Defines Severity of Peri-Prosthetic Regurgitation and Predicts Outcome in Patients After Transcatheter Aortic Valve Implantation. J Am Coll Cardiol (2012). 59(13):1134-1141.
Tonino et al. Fractional Flow Reserve versus Angiography for Guiding Percutaneous Coronary Intervention. New Engl J Med (2009). 360(3):213-224.
Tsai et al. Transcatheter Retrieval of Dislodged Port-A Catheter Fragments: Experience with 47 Cases. Acta Cardiol Sin (2006). 22:221-228.
Van Mieghem et al. Anatomy of the Mitral Valvular Complex and Its Implications for Transcatheter Interventions for Mitral Regurgitation. J Am Coll Cardiol (2010). 56(8):617-626.
PCT/US2014/060526 International Preliminary Report on Patentability dated Apr. 19, 2016, 7 pages.
PCT/US2014/060957 International Preliminary Report on Patentability dated Apr. 19, 2016, 10 pages.
Extended European Search Report for EP Application No. 14853895.2 dated May 10, 2017, 8 pages.
Partial Supplementary European Search Report for EP Application No. 14851950.7 dated Apr. 10, 2017, 6 pages.
Extended European Search Report for EP Application No. 14869869.9 dated May 4, 2017, 7 pages.
PCT/US2016/021866 International Search Report and Written Opinion dated May 23, 2016, 11 pages.
PCT/US2016/021866 International Preliminary Report on Patentability dated Sep. 21, 2017, 9 pages.
EP16762555.7 Supplementary European Search Report dated Oct. 5, 2018, 8 pages.
Crushing. (n.d.) American Heritage Dictionary of the English Language, Fifth Edition, 2011, retrieved from https://thefreedictionary.com/crushing.
Compress. (n.d.) Merriam-Webster, 2018, retrieved from https://www.merriam-webster.com/dictionary/compress.
EP 14851950.7 Extended European Search Report dated Jul. 12, 2017, 10 pages.
EP 14851950.7 Examination Report dated May 24, 2018, 4 pages.
EP 14869869.9 Examination Report dated Jan. 23, 2019, 4 pages.

* cited by examiner

DEVICE TO PERCUTANEOUSLY TREAT HEART VALVE EMBOLIZATION

CROSS-REFERENCE TO RELATED APPLICATIONS

This application is a National Phase of International Application No. PCT/US2014/060966 filed Oct. 16, 2014, which designated the U.S. and that International Application was published under PCT Article 21(2) in English, which also includes a claim of priority under 35 U.S.C. § 119(e) to U.S. provisional patent application No. 61/892,381 filed Oct. 17, 2013, the entirety of which is hereby incorporated by reference.

FIELD OF INVENTION

The present invention generally relates to devices and methods for retrieving an embolized or malpositioned heart valve or foreign bodies from a patient's body.

BACKGROUND OF THE INVENTION

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

When a transcatheter heart valve prosthesis is embolized or malpositioned in an incorrect location, such as the left ventricle, the current solution is often open heart surgery which is invasive and has a high mortality rate. Described herein is a device for recapturing an embolized or malpositioned heart valve percutaneously that does not require open heart surgery. The percutaneous removal of an embolized or malpositioned heart valve using the inventors' device is a safer alternative to conventional open heart surgery.

SUMMARY OF THE INVENTION

The following embodiments and aspects thereof are described and illustrated in conjunction with systems, compositions and methods which are meant to be exemplary and illustrative, not limiting in scope.

In various embodiments, provided herein is a device for retrieving an embolized or malpositioned heart valve or foreign bodies from a patient's heart. In some embodiments, the device comprises: a guide wire; a first component and a second component.

In some embodiments, the first component includes: (i) a first hollow shaft with a first leading end and a first trailing end, wherein the first hollow shaft can be inserted over the guidewire; (ii) a capturing umbrella mounted on the first hollow shaft near or at the first leading end, wherein the capturing umbrella has a compressed or an expanded form and a first delivery catheter housing the first hollow shaft and the capturing umbrella. The capturing umbrella is compressed when the first delivery catheter encloses the capturing umbrella and wherein the capturing umbrella is expanded when the first delivery catheter does not enclose the capturing umbrella.

The second component includes: (i) a second hollow shaft with a second leading end and a second trailing end, wherein the second component can be inserted over the first component's hollow shaft; (ii) a crushing basket mounted on the second hollow shaft near or at the second leading end, wherein the crushing basket has a compressed or an expanded form; (iii) a second delivery catheter housing the second hollow shaft and the crushing basket, wherein the crushing basket is compressed when the second delivery catheter encloses the crushing basket or is expanded when the second delivery catheter does not enclose the crushing basket; and (iv) a control wire. The control wire is connected to the crushing basket and passes through the second hollow shaft, wherein the crushing basket is compressed when the control wire is pulled and expanded when the control wire is not pulled. The openings of the expanded capturing umbrella and the expanded crushing basket face each other.

In some embodiments, the crushing basket and the umbrella may be reversed, the crushing basket may be mounted on the leading end of the first component. Additionally, the umbrella may be mounted on the leading edge of the second component.

Also provided herein are methods of using the above device for retrieving an embolized or malpositioned heart valve or foreign bodies in a patient's heart.

In various embodiments, described herein is a device for retrieving an embolized or malpositioned heart valve or foreign bodies in a patient's heart. The device comprises: a guide wire; a first component and a second component.

The first component comprises: (i) a first hollow shaft with a first leading end and a first trailing end, wherein the first hollow shaft can be inserted over the guidewire; (ii) a capturing umbrella mounted on the first hollow shaft near or at the first leading end, wherein the capturing umbrella has a compressed or an expanded form; and (iii) a first delivery catheter housing the first hollow shaft and the capturing umbrella. The capturing umbrella is compressed when the first delivery catheter encloses the capturing umbrella and is expanded when the first delivery catheter does not enclose the capturing umbrella.

The second component comprises: (i) a second hollow shaft with a second leading end and a second trailing end, wherein the second component can be inserted over the first component's hollow shaft; (ii) a crushing basket mounted on the second hollow shaft near or at the second leading end, wherein the crushing basket has a compressed form and an expanded form; (iii) a second delivery catheter housing the second hollow shaft and the crushing basket, wherein the crushing basket is compressed when the second delivery catheter encloses the crushing basket, and the crushing basket is expanded when the second delivery catheter does not enclose the crushing basket; and (iv) a control wire. The control wire is connected to the crushing basket and passes through the second hollow shaft, wherein the crushing basket is compressed when the control wire is pulled and is expanded when the control wire is not pulled. The openings of the expanded capturing umbrella and the expanded crushing basket face each other.

Also provided herein are methods of using the device above for retrieving an embolized or malpositioned heart valve or foreign bodies in a patient's heart.

In various embodiments, described herein is a device for retrieving an embolized or malpositioned heart valve or foreign bodies in a patient's heart. The device comprises: (i) a guide wire; (ii) a first hollow shaft with a first leading end and a first trailing end, wherein the first hollow shaft can be inserted over the guidewire; (iii) a capturing umbrella mounted on the first hollow shaft near or at the first leading end (or in some embodiments, on the second hollow shaft near or at the second leading end), wherein the capturing umbrella has a compressed form and an expanded form; (iv) a second hollow shaft with a second leading end and a second trailing end, the second hollow shaft houses the first hollow shaft and the capturing umbrella, wherein the capturing umbrella is compressed when the second hollow shaft encloses the capturing umbrella, and wherein the capturing umbrella is expanded when the second hollow shaft does not enclose the capturing umbrella; (v) a crushing basket mounted on the second hollow shaft near or at the second leading end (or in some embodiments, on the first hollow shaft near or at the first leading end), wherein the crushing basket has a compressed form and an expanded form; (vi) a delivery catheter housing the second hollow shaft and the crushing basket, wherein the crushing basket is compressed when the delivery catheter encloses the crushing basket, and wherein the crushing basket is expanded when the delivery catheter does not enclose the crushing basket; and (vii) a control wire, wherein the control wire is connected to the crushing basket and passes through the second hollow shaft, wherein the crushing basket is compressed when the control wire is pulled, and wherein the crushing basket is expanded when the control wire is not pulled; and wherein the openings of the expanded capturing umbrella and the expanded crushing basket face each other.

In some embodiments, the delivery catheter will house and restrain both the crushing basket and the umbrella, and the second hollow shaft will not contain the umbrella or crushing basket.

Also provided herein are methods of using the device above for retrieving an embolized or malpositioned heart valve or foreign bodies in a patient's heart.

BRIEF DESCRIPTION OF FIGURES

Exemplary embodiments are illustrated in the referenced figures. It is intended that the embodiments and figures disclosed herein are to be considered illustrative rather than restrictive.

FIG. 1A illustrates a guide wire 101, a first hollow shaft 102 that has a leading end that can be advanced over the trailing end of a guide wire 101; a capturing umbrella 107 is mounted at or near the leading end of the first hollow shaft 102; and when a first delivery catheter 103 encloses the capturing umbrella 107, the capturing umbrella 107 is compressed. In FIG. 1B, when the first delivery catheter 103 is retracted, the capture umbrella 107 is expanded. In FIG. 1C, the first hollow shaft 102 is inserted into a second hollow shaft 108; a crushing basket 105 is mounted at or near the leading end of the second hollow shaft 108; and when a second delivery catheter 104 encloses the crushing basket 105, the crushing basket 105 is compressed. In FIG. 1D, when the second delivery catheter 104 is retracted, the crushing basket 105 is expanded. In some embodiments, the crushing basket 105 comprises a spiral 109. A control wire 106 is connected to the spiral 109 and passes through the second hollow shaft 108. When the control wire 106 is pulled, the crushing basket 105 is compressed to crush the object engulfed in the crushing basket.

FIGS. 2-9 depict, in accordance with various embodiments of the present invention, cross sectional views of a method for percutaneously retrieving an embolized or malpositioned heart valve in a patient's heart.

FIG. 2 depicts, in accordance with various embodiments of the present invention, a cross sectional view of a guide wire 101 inserted through the ascending aorta into a patient's left ventricle, where a heart valve 301 is embolized or malpositioned, and the guide wire is advanced through or inside the frame or stent of the embolized or malpositioned heart valve. In some embodiments, the guide wire 101 will already be in place and run through the cross section of the heart valve after a embolized or malpositioned heart valve results from a failed attempt at implanting a transcatheter heart valve.

FIG. 4 depicts, in accordance with various embodiments of the present invention, a cross sectional view of the first delivery catheter 103 completely retracted to expand the capturing umbrella 107.

FIG. 5 depicts, in accordance with various embodiments of the present invention, a cross sectional view of the expanded capturing umbrella 107 pulled back to capture the embolized or malpositioned valve 301.

FIG. 7 depicts, in accordance with various embodiments of the present invention, a cross sectional view of the second delivery catheter 104 partially retracted to expand the crushing basket 105.

FIG. 8A depicts three close-up views of three examples of click-and-lock systems.

In FIG. 10A, the first component (including 102, 103 and 107) is inserted into the second component (including 104, 105, 106, and 108). A guide wire 101 is in place and the leading end of the first hollow shaft 102 can be advanced over the trailing end of the guide wire; a capturing umbrella 107 is mounted at or near the leading end of the first hollow shaft 102; and when a first delivery catheter 103 encloses the capturing umbrella 107, the capturing umbrella 107 is compressed. The first delivery catheter is inserted into a second hollow shaft 108; a crushing basket 105 is mounted at or near the leading end of the second hollow shaft 108; and when a second delivery catheter 104 encloses the crushing basket 105, the crush basket 105 is compressed. The first component protrudes outside the second component so that the capturing umbrella 107 is located distal to the crushing basket 105. The device is guided over the guide wire 101 through an embolized or malpositioned valve to be retrieved, until the embolized or malpositioned valve is located between the capturing umbrella 107 and the crushing basket 105. In FIG. 10B, when the first delivery catheter 103 is retracted, the capture umbrella 107 is expanded. In FIG. 10C, when the second delivery catheter 104 is retracted, the crushing basket 105 is expanded. The crushing basket 105 comprises a spiral 109. A control wire 106 is connected to the spiral 109 and threaded through the second hollow shaft 108. When the control wire 106 is pulled, the crushing basket 105 is compressed to crush the crushing basket and objects engulfed in the crushing basket. In FIG. 10D, in some embodiments, the expanded crushing basket 105 and the expanded capturing umbrella 107 are connected to enclose an embolized or malpositioned valve. Various connecting means can be used to connect the openings of the expanded crushing basket 105 and the expanded capturing umbrella 107. Three examples of click-and-lock systems are shown in FIG. 8A. The control wire 106 can be pulled to crush the crushing basket 105, the capturing umbrella 107, and the embolized or malpositioned valve. In FIG. 10E, in other embodiments, the expanded crushing basket engulfs the capturing umbrella and an embolized or malpositioned valve. The expanded crushing basket 105 is configured in sufficient size to accommodate the expanded capturing umbrella 107 together with the captured valve. The control wire 106 can be pulled to crush the crushing basket, the capturing umbrella, and the embolized or malpositioned valve.

FIG. 11 depicts, in accordance with various embodiments of the present invention, cross sectional views of an example where a TAVR device has embolized or malpositioned into the left ventricle. A guide wire 101 is inserted through aorta into a patient's left ventricle, where a heart valve 301 is embolized or malpositioned; the guide wire is advanced through the embolized or malpositioned heart valve 301; the guide wire may, as is more frequently the case, already be in place through the embolized or malpositioned heart valve as transcatheter heart valves are implanted over a guide wire 101; the leading end of the first hollow shaft 102 is advanced over the trailing end of a guide wire 101; until the capturing umbrella 105 passes the embolized or malpositioned valve and until the crushing basket 105 enters the patient's left ventricle but does not pass the embolized or malpositioned valve. As a result, the embolized or malpositioned valve is located between the crushing basket 105 and the capturing umbrella 107 i.e. on the ventricular (proximal) aspect of the crushing basket and on the aortic (distal) aspect of the capturing umbrella.

FIG. 12 depicts, in accordance with various embodiments of the present invention, a cross sectional view of the first delivery catheter 103 completely retracted to expand the capturing umbrella 107, and the second delivery catheter 104 is partially retracted to expand the crushing basket 105.

FIG. 13 depicts, in accordance with various embodiments of the present invention, a cross sectional view of, the expanded crushing basket 105 and the expanded capturing umbrella 107 connected to enclose an embolized or malpositioned valve. Various connecting means can be used to connect the openings of the expanded crushing basket 105 and the expanded capturing umbrella 107. Three examples of click-and-lock systems are shown in FIG. 8A.

FIG. 14 depicts, in accordance with various embodiments of the present invention, a cross sectional view of, the control wire 106 pulled to crush the crushing basket 105, the capturing umbrella 107, and the embolized or malpositioned valve 301. The compressed crushing basket, capturing umbrella, and embolized or malpositioned valve (the crushed objects) are retrieved out of the patient either by pulling the whole system through a sheath or through the second delivery catheter 104. Alternatively, the compressed crushing basket, capturing umbrella, and embolized or malpositioned valve (the crushed objects) are enclosed into the second delivery catheter 104, and retrieved together with the second delivery catheter out of the patient. In some embodiments the crushed objects are not removed from the body but retracted to a safer location such as but not limited to the descending aorta.

In FIG. 15A, a guide wire 201 is inserted into a first hollow shaft 202. A capturing umbrella 207 is mounted at or near the leading end of the first hollow shaft 202. A second hollow shaft 208 encloses the first hollow shaft 202 and the compressed capturing umbrella 207. A crushing basket 205 is mounted at or near the leading end of the second hollow shaft 208. A delivery catheter 204 encloses the second hollow shaft 208 and the compressed crushing basket 205. The crushing basket 205 comprises a spiral 209. A control wire 206 is connected to the spiral 209 and threaded through the second hollow shaft 208. When the control wire 206 is pulled, the crushing basket 205 is compressed to crush the crushing basket 205 and objects engulfed in the crushing basket 205. The device is guided over the guide wire 101 through an embolized or malpositioned valve to be retrieved. In FIG. 15B, when the second hollow shaft 208 is retracted, the first hollow shaft 202 is exposed and the capture umbrella 207 is expanded. In FIG. 15C, when the delivery catheter 204 is refracted, the crushing basket 205 is expanded. In FIG. 15D, in some embodiments, the expanded crushing basket 205 and the expanded capturing umbrella 207 are connected to enclose an embolized or malpositioned valve. Various connecting means can be used to connect the openings of the expanded crushing basket 205 and the expanded capturing umbrella 207. Three examples of click-and-lock systems are shown in FIG. 8A. The control wire 206 can be pulled to crush the crushing basket 205, the capturing umbrella 207, and the embolized or malpositioned valve. In FIG. 15E, in other embodiments, the expanded crushing basket 205 engulfs the capturing umbrella 207 and an embolized or malpositioned valve. The expanded crushing basket 205 is configured in sufficient size to accommodate the expanded capturing umbrella 207 together with the captured valve. The control wire 206 can be pulled to crush the crushing basket, the capturing umbrella, and the embolized or malpositioned valve.

DETAILED DESCRIPTION OF THE INVENTION

Figure 1A:
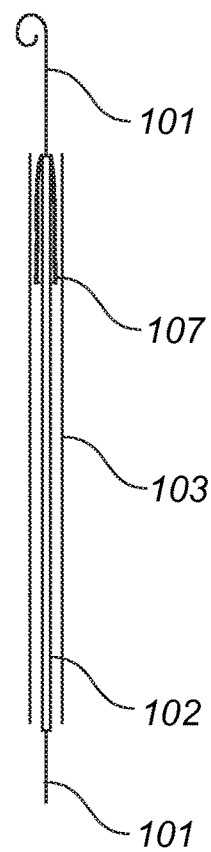
FIGS. 1A-D depict, in accordance with various embodiments of the present invention, a cross sectional views of a device for percutaneously retrieving an embolized or malpositioned heart valve or other foreign bodies in a patient's heart.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure* 5th ed., J. Wiley & Sons (New York, N.Y. 2001); Sambrook and Russel, *Molecular Cloning: A Laboratory Manual* 3rd ed., Cold Spring Harbor Laboratory Press (Cold Spring Harbor, N.Y. 2001); *Szycher's Dictionary of Medical Devices* (1995); and Iaizoon, *Handbook of Cardiac Anatomy, Physiology, and Devices* (2009), provide one skilled in the art with a general guide to many of the terms and phrases used in the present application.

One skilled in the art will recognize many methods and materials similar or equivalent to those described herein, which could be used in the practice of the present invention. Indeed, the present invention is in no way limited to the methods and materials described.

In accordance with the present invention, properties such as dimensions, shapes, relative positions, and so forth, used to describe and claim various embodiments of the invention are to be understood as being modified by the term "about".

In accordance with various embodiments of the present invention, an embolized or malpositioned valve was originally implanted to replace a diseased heart valve, such as aortic valve, mitral valve, pulmonary valve, and tricuspid valve. In accordance with various embodiments of the present invention, the embolized or malpositioned valve is a prosthetic valve or a bio-prosthetic valve. As used herein, a prosthetic valve is made of purely artificial or non-biological materials, while a bioprosthetic valve is made of animal tissues alone or in combination with artificial or non-biological materials. In accordance with various embodiments of the present invention, the embolized or malpositioned valve can be self-expandable or balloon-expandable. Examples of self-expandable valves include, but are not limited to, MEDTRONIC COREVALVE, which is constructed with a nitinol self-expanding valve stent frame and porcine pericardial leaflets. Examples of balloon-expandable valves include, but are not limited to, EDWARDS SAPIEN XT valve, which is constructed with a cobalt-chromium balloon-expandable valve stent frame and bovine pericardial leaflets.

In various embodiments, the present invention provides for a device for retrieving an embolized or malpositioned heart valve or foreign bodies in a patient's heart. The device comprises: a guide wire; a first component and a second component. The first component comprises: a first hollow shaft with a first leading end and a first trailing end, wherein the leading end of the first hollow shaft is advanced over the trailing end of a guide wire; a capturing umbrella mounted on the first hollow shaft near or at the first leading end, wherein the capturing umbrella has a compressed form and an expanded form; and a first delivery catheter housing the first hollow shaft and the capturing umbrella, wherein the capturing umbrella is compressed when the first delivery catheter encloses the capturing umbrella, and wherein the capturing umbrella is expanded when the first delivery catheter does not enclose the capturing umbrella. The second component comprises: a second hollow shaft with a second leading end and a second trailing end, wherein the first hollow shaft can be inserted into the second hollow shaft; a crushing basket mounted on the second hollow shaft near or at the second leading end, wherein the crushing basket has a compressed form and an expanded form; a second delivery catheter housing the second hollow shaft and the crushing basket, wherein the crushing basket is compressed when the second delivery catheter encloses the crushing basket, and wherein the crushing basket is expanded when the second delivery catheter does not enclose the crushing basket; and a control wire, wherein the control wire is connected to the crushing basket and is threaded through the second hollow shaft, wherein the crushing basket is compressed when the control wire is pulled, and wherein the crushing basket is expanded when the control wire is not pulled; and wherein the openings of the expanded capturing umbrella and the expanded crushing basket face each other.

Capturing Umbrella

In accordance with the present invention, the expanded capturing umbrella can capture an embolized or malpositioned valve. In various embodiments, the capturing umbrella comprises a frame. In various embodiments, the capturing umbrella comprises a mesh. In some embodiments, the frame or mesh can be made of a memory metal. In some embodiments, the frame or mesh can be made of iron, platinum, titanium, nickel, chromium, cobalt, stainless steel, nitinol (nickel-titanium), nickel-chromium, or cobalt-chromium, or a combination thereof. In various embodiments, the compressed capturing umbrella can adopt a cylindrical shape. In various embodiments, the expanded capturing umbrella can adopt a cone-like shape.

Crushing Basket

In various embodiments, the crushing basket comprises a spiral. In some embodiments the basket may comprise multiple interconnected rings. In some embodiments, the spiral or multiple interconnected rings can be made of iron, platinum, titanium, nickel, chromium, cobalt, stainless steel, nitinol (nickel-titanium), nickel-chromium, or cobalt-chromium, or a combination thereof. In various embodiments, the compressed crushing basket can adopt a cylindrical shape. In various embodiments, the expanded crushing basket can adopt a cone-like shape.

In various embodiments, the control wire is made of iron, platinum, titanium, nickel, chromium, cobalt, stainless steel, nitinol (nickel-titanium), nickel-chromium, or cobalt-chromium, or a combination thereof.

In various embodiments, the expanded crushing basket can engulf the expanded capturing umbrella, and when the control wire is pulled, the capturing umbrella and the crushing basket are both compressed. As a result, an embolized or malpositioned valve or foreign object enclosed in the capturing umbrella and the crushing basket is crushed.

In various embodiments, the present invention provides for a method of using a device as described above for retrieving an embolized or malpositioned heart valve or foreign bodies in a patient's heart. The method comprises the following steps: (1) providing a device of as described above; (2) inserting a guide wire into a patient's heart chamber, where a heart valve is embolized or malpositioned; (3) advancing the guide wire through the embolized or malpositioned heart valve, or using a wire already present through the embolized or malpositioned heart valve; (4) advancing the first component over the guide wire until the capturing umbrella passes the embolized or malpositioned valve; (5) retracting the first delivery catheter to expand the capturing umbrella; (6) advancing the second component over the first hollow shaft until the crushing basket enters the patient's heart chamber but does not pass the embolized or malpositioned valve; (7) retracting the second delivery catheter to expand the crushing basket; (8) using the expanded crushing basket to engulf the capturing umbrella and the embolized or malpositioned valve; and (9) pulling the control wire to compress the crushing basket, the capturing umbrella, and the embolized or malpositioned valve.

When trying to use the expanded crushing basket to engulf the capturing umbrella and the embolized or malpositioned valve, one could take a variety of maneuvers, including but not limited to, advancing the crushing basket toward the capturing umbrella, or retracting the capturing umbrella toward the crushing basket, or simultaneously advancing the crushing basket and retracting the capturing umbrella toward each other. In some embodiments, the method further comprises retrieving the compressed crushing basket, capturing umbrella, and embolized or malpositioned valve out of the patient through the second delivery catheter. In other embodiments, the method further comprise enclosing the compressed crushing basket, capturing umbrella, and embolized or malpositioned valve into the second delivery catheter; and retrieving the second delivery catheter together with the compressed crushing basket, capturing umbrella, and embolized or malpositioned valve out of the patient. When trying to enclose the compressed crushing basket, capturing umbrella, and embolized or malpositioned valve (i.e., the crushed objects) into the second delivery catheter, one could take a variety of maneuvers, including but not limited to, advancing the second delivery catheter toward the crushed objects, or retracting the crushed objects toward the second delivery catheter, or simultaneously advancing the second delivery catheter and retracting the crushed objects toward each other.

Figure 8A:
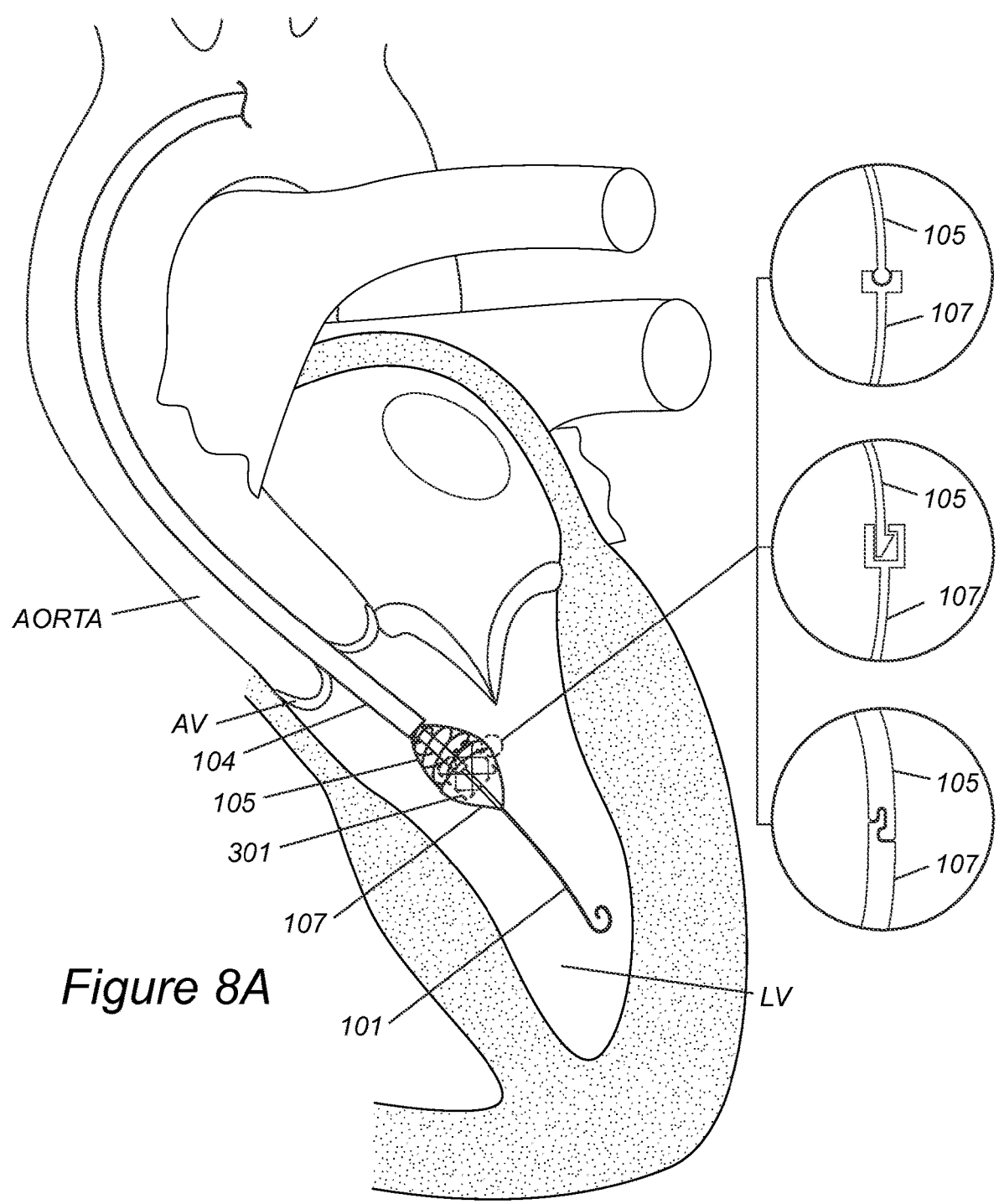
FIG. 8A depicts, in accordance with various embodiments of the present invention, the expanded crushing basket 105 and the expanded capturing umbrella 107 connected to enclose the embolized or malpositioned valve 301. Various connecting means can be used to connect the openings of the expanded crushing basket 105 and the expanded capturing umbrella 107.

In various embodiments, the device further comprises a connecting means for connecting the openings of the expanded capturing umbrella and the expanded crushing basket. Examples of the connecting means include, but are not limited to, a click-and-lock system, interlocking structures, clasps, hooks, rings, bolts, nuts, screws, nails, fasteners, magnets, mortises and tenons, and other similar structures. Exemplary connecting means are depicted in FIG. 8A. Other examples may be found in US 2010/0185275 A1 and U.S. Pat. No. 5,250,071, which are incorporated herein by reference as a whole. In various embodiments, when their openings are connected and the control wire is pulled, the capturing umbrella and the crushing basket are both compressed. As a result, an embolized or malpositioned valve or foreign object enclosed in the capturing umbrella and the crushing basket is crushed.

In various embodiments, the present invention provides for a method of using a device as described above for retrieving an embolized or malpositioned heart valve or foreign bodies in a patient's heart. The method comprises the following steps: (1) providing a device as described above; (2) inserting a guide wire into a patient's heart chamber, where a heart valve is embolized or malpositioned; (3) advancing the guide wire through the embolized or malpositioned heart valve, or using a guide wire already positioned through the embolized or malpositioned heart valve; (4) advancing the first component over the guide wire until the capturing umbrella passes the embolized or malpositioned valve; (5) retracting the first delivery catheter to expand the capturing umbrella; (6) advancing the second component over the first hollow shaft until the crushing basket enters the patient's heart chamber but does not pass the embolized or malpositioned valve; (7) retracting the second delivery catheter to expand the crushing basket; (8) connecting the expanded crushing basket and the expanded capturing umbrella to enclose the embolized or malpositioned valve; and (9) pulling the control wire to compress the crushing basket, the capturing umbrella, and the embolized or malpositioned valve.

When trying to connect the expanded crushing basket and the expanded capturing umbrella to enclose the embolized or malpositioned valve, one could take a variety of maneuvers, including but not limited to, advancing the crushing basket toward the capturing umbrella, or retracting the capturing umbrella toward the crushing basket, or simultaneously advancing the crushing basket and retracting the capturing umbrella toward each other. In some embodiments, the method further comprises retrieving the compressed crushing basket, capturing umbrella, and embolized or malpositioned valve out of the patient through the second delivery catheter. In other embodiments, the method further comprise enclosing the compressed crushing basket, capturing umbrella, and embolized or malpositioned valve into the second delivery catheter; and retrieving the second delivery catheter together with the compressed crushing basket, capturing umbrella, and embolized or malpositioned valve out of the patient. When trying to enclose the compressed crushing basket, capturing umbrella, and embolized or malpositioned valve (i.e., the crushed objects) into the second delivery catheter, one could take a variety of maneuvers, including but not limited to, advancing the second delivery catheter toward the crushed objects, or retracting the crushed objects toward the second delivery catheter, or simultaneously advancing the second delivery catheter and retracting the crushed objects toward each other.

In various embodiments, the present invention provides for a device for retrieving an embolized or malpositioned heart valve or foreign bodies in a patient's heart. The device comprises: a guide wire; a first component and a second component. The first component comprises: a first hollow shaft with a first leading end and a first trailing end, wherein the leading end of the first hollow shaft can be advanced over the trailing end of a guide wire; a capturing umbrella mounted on the first hollow shaft near or at the first leading end, wherein the capturing umbrella has a compressed form and an expanded form; and a first delivery catheter housing the first hollow shaft and the capturing umbrella, wherein the capturing umbrella is compressed when the first delivery catheter encloses the capturing umbrella, and wherein the capturing umbrella is expanded when the first delivery catheter does not enclose the capturing umbrella. The second component comprises: a second hollow shaft with a second leading end and a second trailing end, wherein the first component can be inserted in the second hollow shaft; a crushing basket mounted on the second hollow shaft near or at the second leading end, wherein the crushing basket has a compressed form and an expanded form; a second delivery catheter housing the second hollow shaft and the crushing basket, wherein the crushing basket is compressed when the second delivery catheter encloses the crushing basket, and wherein the crushing basket is expanded when the second delivery catheter does not enclose the crushing basket; and a control wire, wherein the control wire is connected to the crushing basket and passes through the second hollow shaft, wherein the crushing basket is compressed when the control wire is pulled, and wherein the crushing basket is expanded when the control wire is not pulled; and wherein the openings of the expanded capturing umbrella and the expanded crushing basket face each other. In some embodiments, the two components are not assembled together. In other embodiments, the first component is inserted into the second component and both components are advanced together over the guide wire.

In various embodiments, the expanded crushing basket can engulf the expanded capturing umbrella, and when the control wire is pulled, the capturing umbrella and the crushing basket are both compressed. As a result, an embolized or malpositioned valve or foreign object enclosed in the capturing umbrella and the crushing basket is crushed. In various embodiments, the present invention provides for a method of using a device as described above for retrieving an embolized or malpositioned heart valve or foreign bodies in a patient's heart. The method comprises the following steps: (1) providing a device as described above; (2) inserting a guide wire into a patient's heart chamber, where a heart valve is embolized or malpositioned; (3) advancing the guide wire through the embolized or malpositioned heart valve; (4) advancing the first component over the guide wire until the capturing umbrella passes the embolized or malpositioned valve; (5) advancing the second component over the first component until the crushing basket enters the patient's heart chamber but does not pass the embolized or malpositioned valve; (6) retracting the first delivery catheter to expand the capturing umbrella; (7) retracting the second delivery catheter to expand the crushing basket; (8) using the expanded crushing basket to engulf the capturing umbrella and the embolized or malpositioned valve; and (9) pulling the control wire to compress the crushing basket, the capturing umbrella, and the embolized or malpositioned valve.

In various embodiments, the device further comprises a connecting means for connecting the openings of the expanded capturing umbrella and the expanded crushing basket. In various embodiments, when their openings are connected and the control wire is pulled, the capturing umbrella and the crushing basket are both compressed. As a result, an embolized or malpositioned valve or foreign object enclosed in the capturing umbrella and the crushing basket is crushed. In various embodiments, the present invention provides for a method of using a device as described above for retrieving an embolized or malpositioned heart valve or foreign bodies in a patient's heart. The method comprises the following steps: (1) providing a device of as described above; (2) inserting a guide wire into a patient's heart chamber, where a heart valve is embolized or malpositioned; (3) advancing the guide wire through the embolized or malpositioned heart valve or using a guide wire already positioned through the embolized or malpositioned heart valve; (4) advancing the first component over the guide wire until the capturing umbrella passes the embolized or malpositioned valve; (5) advancing the second component over the first component until the crushing basket enters the patient's heart chamber but does not pass the embolized or malpositioned valve; (6) retracting the first delivery catheter to expand the capturing umbrella; (7) retracting the second delivery catheter to expand the crushing basket; (8) connecting the expanded crushing basket and the expanded capturing umbrella to enclose the embolized or malpositioned valve; and (9) pulling the control wire to compress the crushing basket, the capturing umbrella, and the embolized or malpositioned valve.

In various embodiments, the present invention provides for a device for retrieving an embolized or malpositioned heart valve or foreign bodies in a patient's heart. The device comprises: a guide wire; a first hollow shaft with a first leading end and a first trailing end, wherein the leading end of the first hollow shaft can be advanced over the trailing end of a guide wire; a capturing umbrella mounted on the first hollow shaft near or at the first leading end, wherein the capturing umbrella has a compressed form and an expanded form; a second hollow shaft with a second leading end and a second trailing end, the second hollow shaft houses the first hollow shaft and the capturing umbrella, wherein the capturing umbrella is compressed when the second hollow shaft encloses the capturing umbrella, and wherein the capturing umbrella is expanded when the second hollow shaft does not enclose the capturing umbrella; a crushing basket mounted on the second hollow shaft near or at the second leading end, wherein the crushing basket has a compressed form and an expanded form; a delivery catheter housing the second hollow shaft and the crushing basket, wherein the crushing basket is compressed when the delivery catheter encloses the crushing basket, and wherein the crushing basket is expanded when the delivery catheter does not enclose the crushing basket; and a control wire, wherein the control wire is connected to the crushing basket and is threaded through the second hollow shaft, wherein the crushing basket is compressed when the control wire is pulled, and wherein the crushing basket is expanded when the control wire is not pulled; and wherein the openings of the expanded capturing umbrella and the expanded crushing basket face each other.

In various embodiments, the expanded crushing basket can engulf the expanded capturing umbrella, and when the control wire is pulled, the capturing umbrella and the crushing basket are both compressed. As a result, an embolized or malpositioned valve or foreign object enclosed in the capturing umbrella and the crushing basket is crushed. In various embodiments, the present invention provides for a method of using a device as described above for retrieving an embolized or malpositioned heart valve or foreign bodies in a patient's heart. The method comprises the following steps: (1) providing a device as described above; (2) inserting a guide wire into a patient's heart chamber, where a heart valve is embolized or malpositioned; (3) advancing the guide wire through the embolized or malpositioned heart valve or using a guide wire already positioned through an embolized or malpositioned valve; (4) advancing the device over the guide wire, wherein the guide wire is inserted into the first hollow shaft, until the capturing umbrella passes the embolized or malpositioned valve and until the crushing basket enters the patient's heart chamber but does not pass the embolized or malpositioned valve; (5) retracting the second hollow shaft to expand the capturing umbrella; (6) retracting the delivery catheter to expand the crushing basket; (7) using the expanded crushing basket to engulf the capturing umbrella and the embolized or malpositioned valve; and (8) pulling the control wire to compress the crushing basket, the capturing umbrella, and the embolized or malpositioned valve.

In various embodiments, the device further comprises a connecting means for connecting the openings of the expanded capturing umbrella and the expanded crushing basket. In various embodiments, when their openings are connected and the control wire is pulled, the capturing umbrella and the crushing basket are both compressed. As a result, an embolized or malpositioned valve or foreign object enclosed in the capturing umbrella and the crushing basket is crushed. In various embodiments, the present invention provides for a method of using a device as described above for retrieving an embolized or malpositioned heart valve or foreign bodies in a patient's heart. The method comprises the following steps: (1) providing a device of as described above; (2) inserting a guide wire into a patient's heart chamber, where a heart valve is embolized or malpositioned; (3) advancing the guide wire through the embolized or malpositioned heart valve or using a guide wire already positioned through the embolized or malpositioned heart valve; (4) advancing the device over the guide wire, wherein the guide wire is inserted into the first hollow shaft, until the capturing umbrella passes the embolized or malpositioned valve and until the crushing basket enters the patient's heart chamber but does not pass the embolized or malpositioned valve; (5) retracting the second hollow shaft to expand the capturing umbrella; (6) retracting the delivery catheter to expand the crushing basket; (7) connecting the expanded crushing basket and the expanded capturing umbrella to enclose the embolized or malpositioned valve; and (8) pulling the control wire to compress the crushing basket, the capturing umbrella, and the embolized or malpositioned valve.

In various embodiments, a catheter is made of a material that may include, but is not limited to, plastic, hydrophilic material, polyester, and the like. In various embodiments, a catheter can be from 90 to 300 cm long, with a diameter ranging from 2 to 24 French (Fr).

In various embodiments, a hollow shaft is made of a material that may include, but is in no way limited to, plastic, hydrophilic material, polyester, and the like. In various embodiments, a hollow shaft can be from 90 to 300 cm long, with a diameter ranging from 2 to 24 French (Fr).

FIGS. 1A-D depict, in accordance with various embodiments of the present invention, cross sectional views of a device for percutaneously retrieving an embolized or malpositioned heart valve or other foreign bodies in a patient's heart. In this embodiment, the first component is advanced, the umbrella 107 is deployed, and the first delivery catheter 103 is completely retracted before the second component that includes the crushing basket 105 is inserted over the guidewire 101. FIG. 1A illustrates a guide wire 101, a first hollow shaft 102 that has a leading end that can be advanced over a guide wire 101. In some embodiments, a capturing umbrella 107 is mounted at or near the leading end of the first hollow shaft 102, including at the very tip, 2, 3, 4 or mm from the tip, or other suitable distances. In some embodiments prior to delivery of the device, a first delivery catheter 103 is fed over the first hollow shaft 102 in and over the capturing umbrella 107, enclosing and compressing the capturing umbrella 107 to have a slim profile inside the first delivery catheter 103. Accordingly, once the first component illustrated in FIG. 1A is delivered, the delivery catheter 103 may be removed.

Figure 1B:
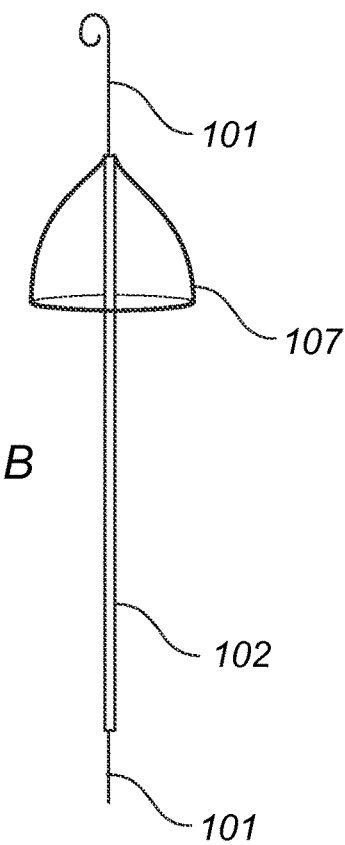

As illustrated in FIG. 1B, removal of the delivery catheter 103, will allow the capturing umbrella 107 to spring out in preparation for capturing the valve. This is because the umbrella 107 may be constructed or manufactured from shape memory metal (e.g. nitinol) with the expanded form as the un-tensioned, natural state. Accordingly, when the delivery catheter 103 is removed, the shape memory material will cause the umbrella 107 to expand and open for capturing of the valve. In some embodiments, instead of the umbrella 107 being compressed a control wire may be retracted or actuated to expand the umbrella 107.

In some embodiments, the umbrella 107 may have struts or a metal nitinol frame, that provide the shape memory characteristics to allow the umbrella to open when the delivery catheter 103 is removed. In some embodiments, the frame or struts may have different geometries and constructions. In some embodiments, the umbrella 107 may be constructed similar to a rain umbrella, with metal struts that radiate out straight from the center, or in a curved or other fashion. In other embodiments, the struts may radiate out from the center and contact a circular, square or other shaped frame that loops around the edges of the umbrella 107. In some embodiments, the struts may stand alone without additional materials on the umbrella 107. In those embodiments, the struts may be positioned close enough together to capture a valve. In other embodiments, nylon mesh, or other materials may form webbing in between the struts. This embodiment may have the advantage of having less metal inserted into the body.

Figure 1C:
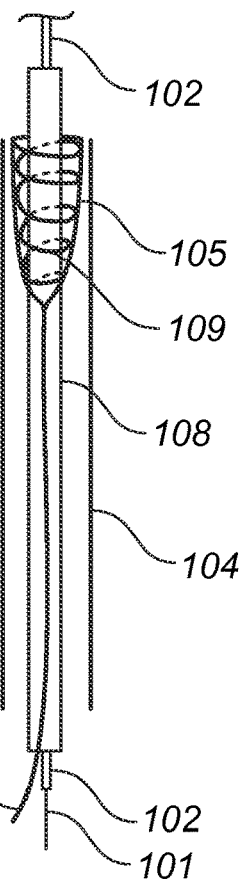
Figure 1D:
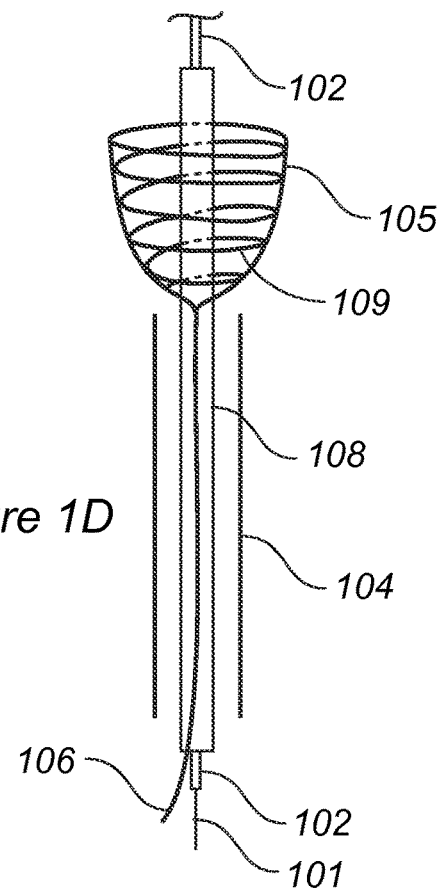

FIG. 1C-1D illustrate an embodiment of the second component of the delivery device, that in some embodiments, will be advanced over the guidewire 101 after the first delivery catheter 103 is removed and the umbrella 107 has expanded. FIG. 1C illustrates the second component assembled in a position for delivery. Illustrated is the first hollow shaft 102 inserted into a second hollow shaft 108; a crushing basket 105 mounted at or near the leading end of the second hollow shaft 108, with a second delivery catheter 104 enclosing the crushing basket 105, compressing the crushing basket 105 into a slim profile.

In some embodiments, the crushing basket 105 may be constructed or manufactured out of shape memory metal that forms a frame similar to that disclosed for the umbrella 107. This will allow the crushing basket 105 to expand when a delivery catheter is removed from on top of it. In some embodiments, the frame will be naturally in the expanded form. In other embodiments, a separate control wire may expand or open the crushing basket 105. The frame of the crushing basket 105 may take a variety of forms as also disclosed with respect to the umbrella 107. This may include straight, curved, or angled, ribs or struts, or struts that fan out at different angles, and other potential arrangements that would allow the frame to expand once the second delivery catheter 104 is removed.

As depicted in FIG. 1D, the second delivery catheter 104 may be refracted after delivery of the second component to the heart, in order to expand the crushing basket 105. In some embodiments, the crushing basket 105 comprises a spiral 109. A control wire 106 is connected to the spiral 109 and passes through the second hollow shaft 108. When the control wire 106 is pulled, the crushing basket 105 is compressed to crush the object engulfed in the crushing basket. This is because the control wire 106 will cause the spiral 109 to become smaller and close around the heart valve. In some embodiments, use of a control wire 106 will be advantageous because the mechanical advantage of distance and force will be utilized to more easily crush a valve. In some embodiments, the spiral 109 will be constructed from a wire or polymer line that will be connected to the frame of the crushing basket 105. In some embodiments, the spiral 109 may be looped through eyelets connected to the frame struts that when the control wire 106 is retracted, the spiral 109 line may move with respect to the frame, to more easily tighten and crush the valve. A designer of catheters may implement several different designs for the spiral 109 in order to utilize the mechanical advantage of the corkscrew type simple machine to crush the valve. In some embodiments, several different control wires 106, which may link to different spirals 109, and can all be retracted to crush the valve.

In some embodiments, the control wire 106 will be connected to a different configuration of wires or mechanism to compress the crushing basket 105 and valve when the control wire 106 is retracted. This could include various mechanical or electromechanical mechanisms, including levers, pulleys, gears, or other mechanism to collapse the frame. In some embodiments, there may be more than one control wire 106 to collapse the crushing basket 105 in different stages. For instance, the most distal end of the crushing basket 105 may be deployed first to ensure that the valve is not squeezed out of the crushing basket 105. Then a separate control wire 106 may be deployed to squeeze the remaining portion of crushing basket 105. Additionally, pulleys may be employed to redirect the control wires 106 in different directions as necessary. In some embodiments, when the control wire 106 is pulled, the control wire's force is directed or multiplied with pulleys and/or gears in order to retract or collapse a frame of the crushing basket 105. This may be facilitated by rotating a knob or by sliding a lever on a delivery system handle.

FIGS. 2-9 depict, in accordance with various embodiments of the present invention, cross sectional views of a method for percutaneously retrieving an embolized or malpositioned heart valve in a patient's heart.

Figure 2:
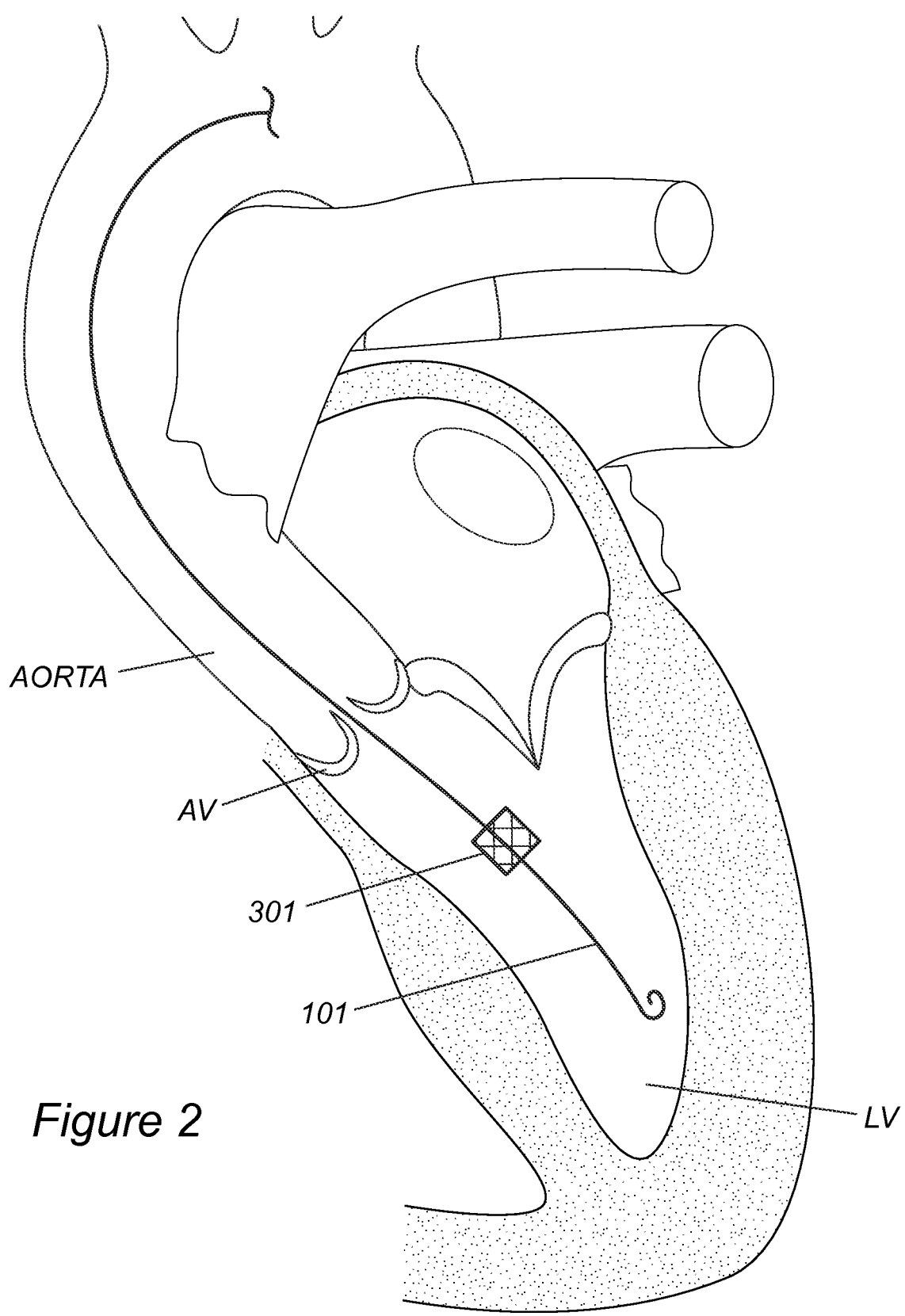

FIG. 2 depicts, in accordance with various embodiments of the present invention, a cross sectional view of a guide wire 101 inserted through the ascending aorta into a patient's left ventricle, where a heart valve 301 is embolized or malpositioned, and the guide wire is advanced through or inside the frame or stent of the embolized or malpositioned heart valve. A operator therefore guides the guidewire 101 so that the curved end passes through the lumen of the prosthetic valve. In some embodiments, the guidewire 101 will have a smaller or triangular shaped end that in some embodiments, is not sharp, but provides a more focused blunt end to guide the tip through the valve. In some embodiments, the guide wire 101 will already be in place and run through the cross section of the heart valve after a failed attempt at a transcatheter heart valve implantation results in an embolized or malpositioned heart valve.

Figures 3A, 3B:
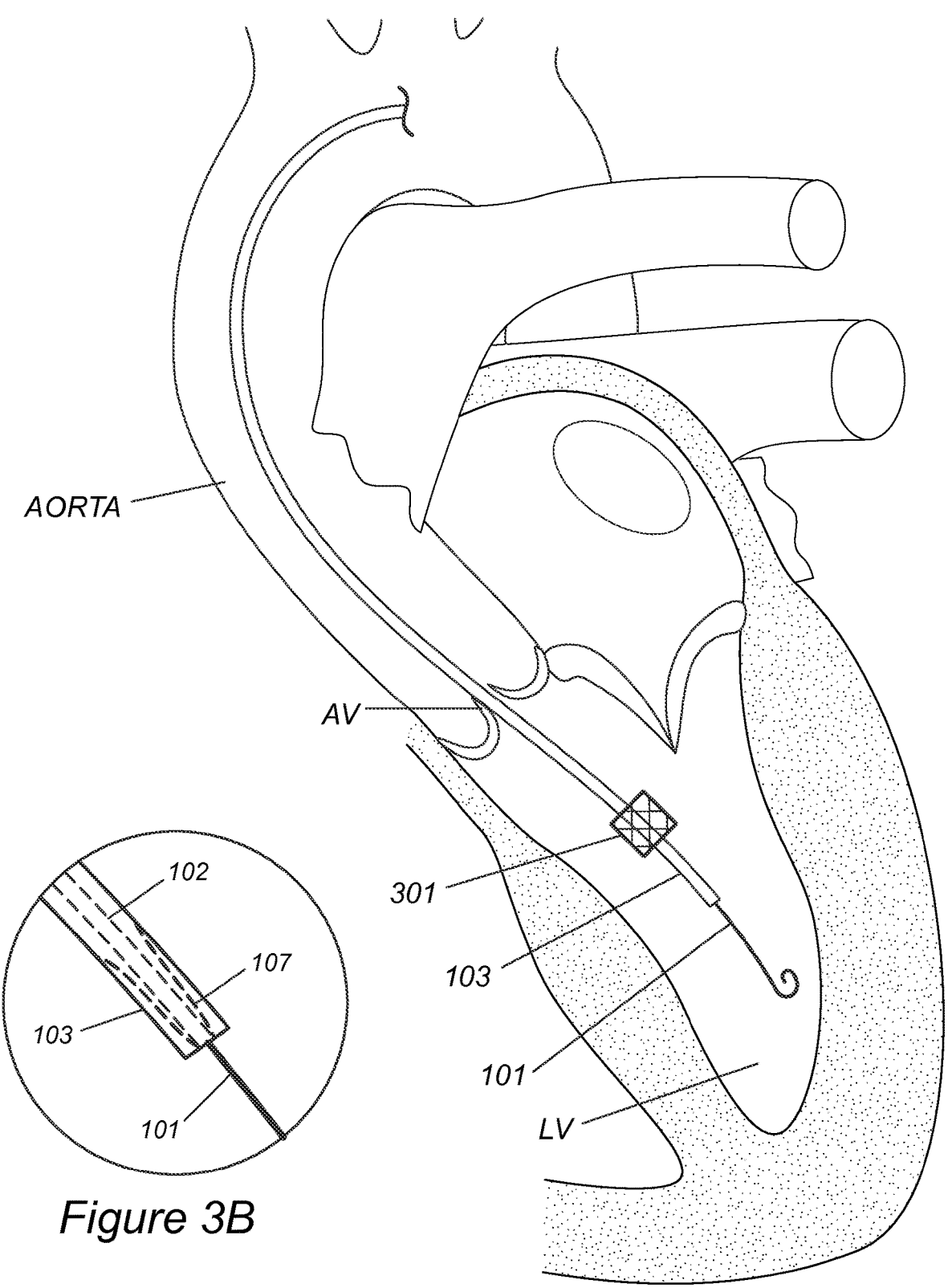
FIG. 3A depicts, in accordance with various embodiments of the present invention, a cross sectional view of the first component advanced over the guide wire 101 into the left ventricle until the capturing umbrella 107 passes the embolized or malpositioned valve.
FIG. 3B depicts a cross sectional close up view of the capturing umbrella 107 restrained inside the first delivery catheter 103.

FIG. 3A depicts, in accordance with various embodiments of the present invention, a cross sectional view of the first component advanced over the guide wire 101 into the left ventricle until the capturing umbrella 107 passes the embolized or malpositioned valve. The first component may include the first delivery catheter 103, the first hollow tube 102, and the umbrella 107. The first component, guided by the first delivery catheter 103, may be passed through the embolized or malpositioned valve over the guidewire 101 so that the umbrella passes or is distal to the valve. FIG. 3B depicts a cross sectional close up view of the capturing umbrella 107 restrained inside the first delivery catheter 103. FIG. 3B depicts the umbrella 107 being restrained and compressed within the first delivery catheter 107. Once in place, the first delivery catheter 107 may be removed to allow the umbrella 107 to expand and deploy. Then, the umbrella 107 will remain attached to the first hollow tube 102 while expanded and open.

Figure 4:
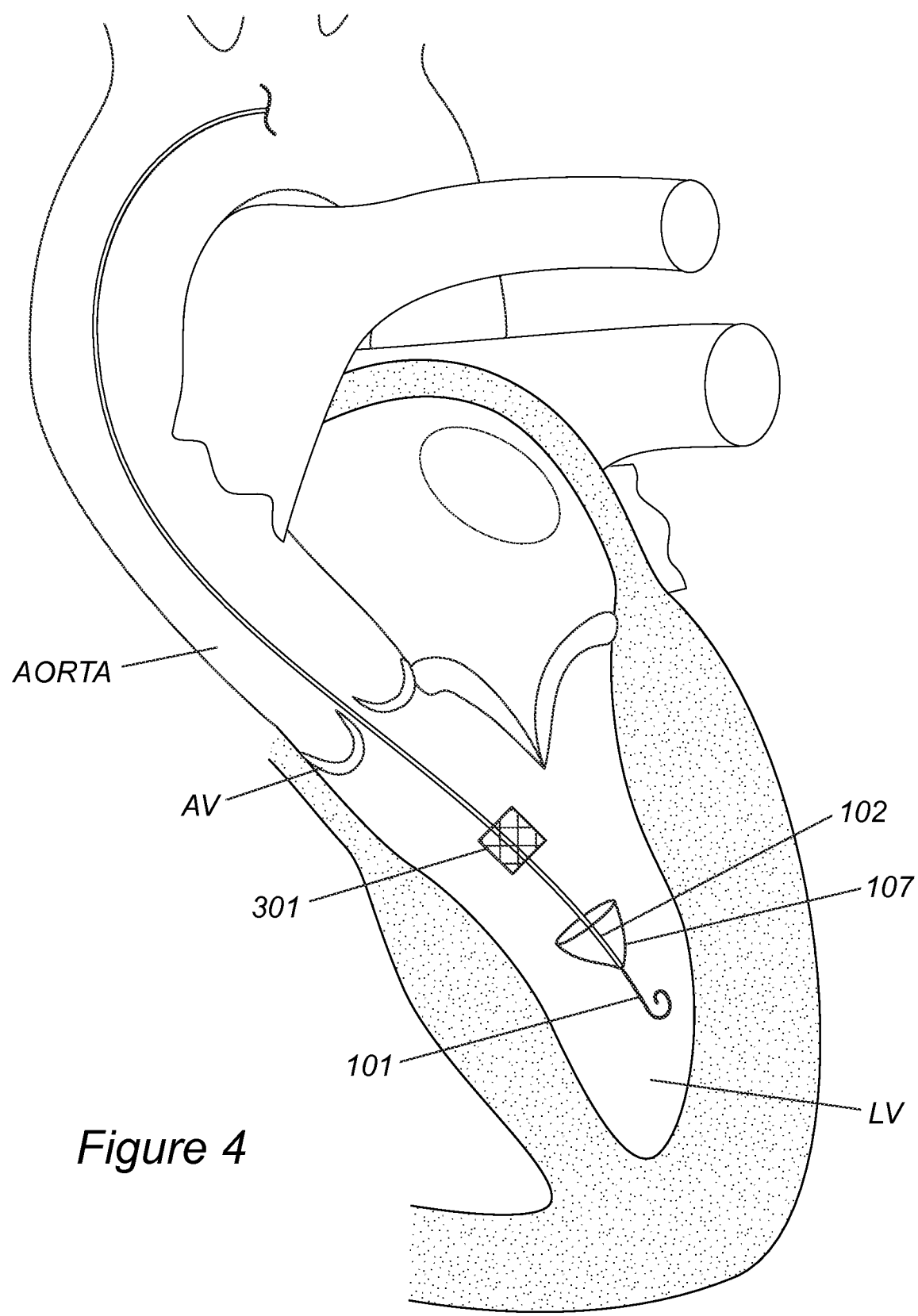

FIG. 4 depicts, in accordance with various embodiments of the present invention, a cross sectional view of the first delivery catheter 103 completely retracted to expand the capturing umbrella 107. FIG. 4 is an embodiment where first delivery catheter 103 has been retracted and removed, allowing umbrella 107 to expand into an open state.

Figure 5:
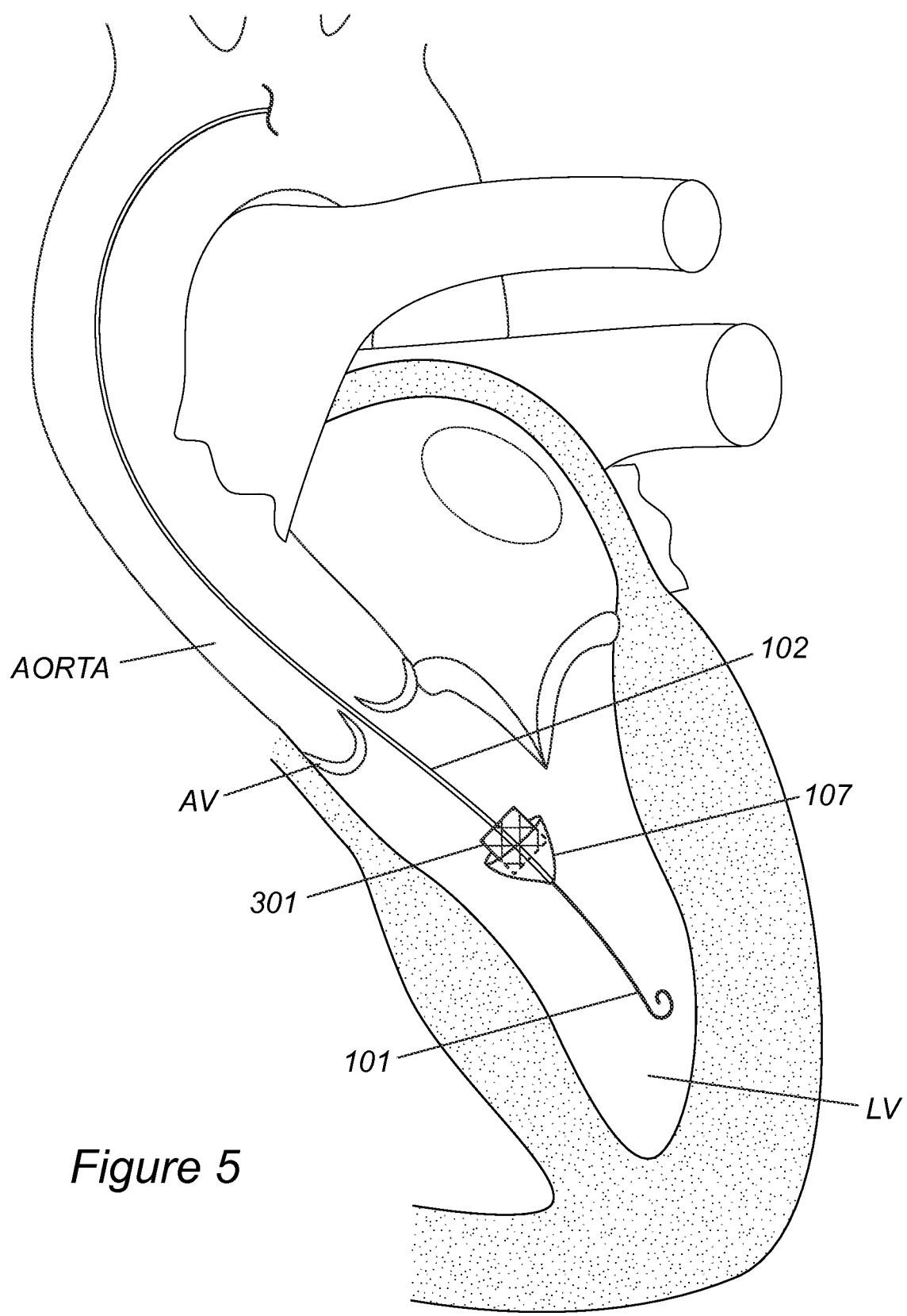

FIG. 5 depicts, in accordance with various embodiments of the present invention, a cross sectional view of the expanded capturing umbrella 107 pulled back to capture the embolized or malpositioned valve 301. In some embodiments, the hollow tube 102 may be retracted along the guidewire 101 so that the umbrella 107 frame will fit around the valve. In some embodiments, as disclosed herein, the umbrella 107 may also be a crushing basket 105, instead. In those embodiments, the same process may be used, and the control wire 106 may be refracted at this step, or at a later step when the second portion is inserted.

Figures 6A, 6B:
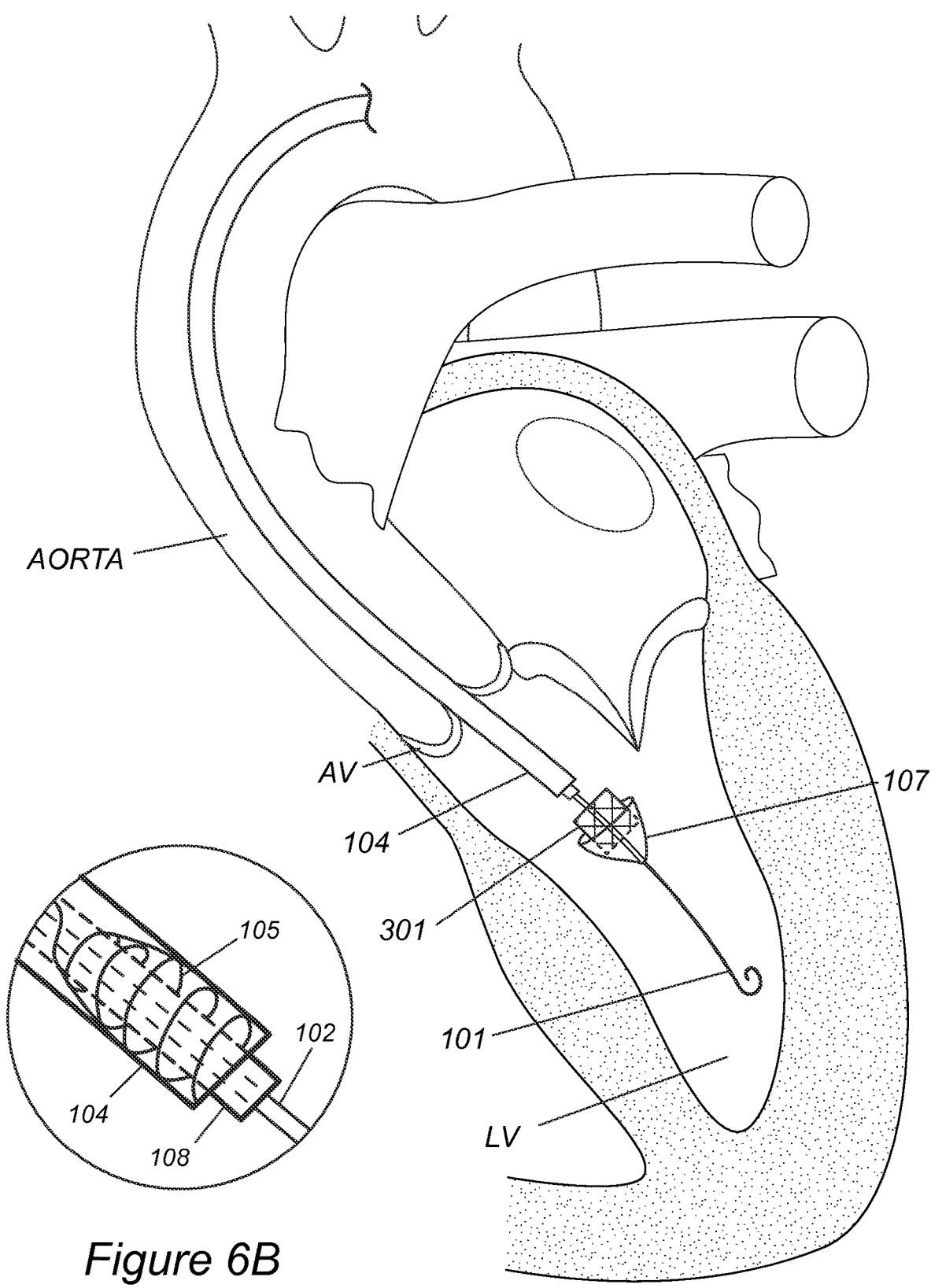
FIG. 6A depicts, in accordance with various embodiments of the present invention, a cross sectional view of the second component advanced over the first hollow shaft 102, until the crushing basket 105 enters the patient's left ventricle but does not pass the embolized or malpositioned valve 301.
FIG. 6B depicts a cross sectional close up view of the crushing basket 105 restrained inside the second delivery catheter 104.

FIG. 6A depicts, in accordance with various embodiments of the present invention, a cross sectional view of the second component advanced over the first hollow shaft 102, until the crushing basket 105 enters the patient's left ventricle but does not pass the embolized or malpositioned valve 301. This positions the second component so that the crushing basket 105 may be expanded once it has passed the aortic valve. FIG. 6B depicts a cross sectional close up view of the crushing basket 105 restrained inside the second delivery catheter 104. As illustrated, the crushing basket 105 is restrained and compressed inside the second delivery catheter 104. Additionally, the crushing basket 105 is fixed to the second hollow tube 108.

Figure 7:
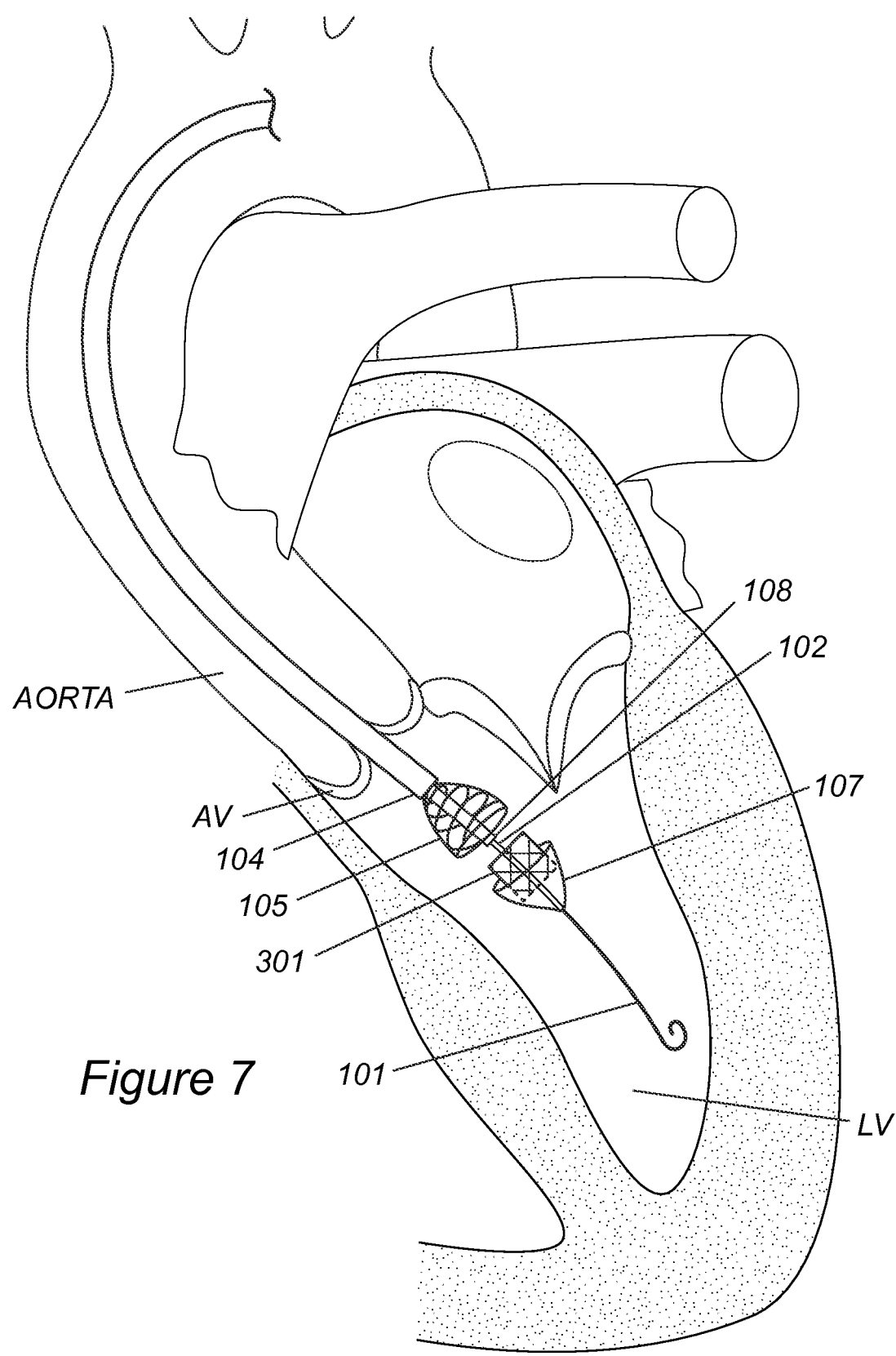

FIG. 7 depicts, in accordance with various embodiments of the present invention, a cross sectional view of the second delivery catheter 104 partially retracted to expand the crushing basket 105. In this embodiment, the caregiver may retract the first delivery catheter 104, in order to expand the crushing basket 105.

FIG. 8A depicts, in accordance with various embodiments of the present invention, the expanded crushing basket 105 and the expanded capturing umbrella 107 connected to enclose the embolized or malpositioned valve 301. In this embodiment, after the crushing basket 105 has been expanded, the operator may either push the second hollow tube 108 further distally, so the crushing basket 105 moves towards the umbrella 107 and traps the embolized or malpositioned valve in between. In other embodiments, the first hollow tube 102 may be retracted to pull the umbrella 105 towards the crushing basket 105 while pushing the valve towards the crushing basket 105. At some point, the crushing basket 105 and the umbrella 107 will then meet, with the open ends touching. In some embodiments, the crushing basket 105 may enclose the umbrella 105. In this embodiment, the crushing basket will crush both the valve and compress the umbrella struts 105. In this embodiment, the radius of the opening of the crushing basket 105 will be larger than the radius of the umbrella 105 and formed so that it would fit inside so both the valve and umbrella 105 may be compressed.

In some embodiments, instead of the crushing basket 105 merely enclosing the umbrella 105, the opening of the crushing basket 105 may be connected to the opening of the umbrella 107 in the left ventricle or other cavities inside the body (depending on the embolized or malpositioned valve type being retrieved). Various connecting means can be used to connect the openings of the expanded crushing basket 105 and the expanded capturing umbrella 107. In FIG. 8A, three close-up views, of three examples of click-and-lock systems are illustrated. The various connections illustrated may be pressure snap fit type connections that when the openings of the umbrella 107 and the crushing basket 105 are pressed against each other, for example by retracting the first hollow tube 102 and or pushing on the second hollow tube 108. This will allow the locking mechanisms to be pushed together so that they snap into the connection and then are retained. Some examples of these types of connections are illustrated in FIG. 8A's three close of views of the connections.

Figure 8B:
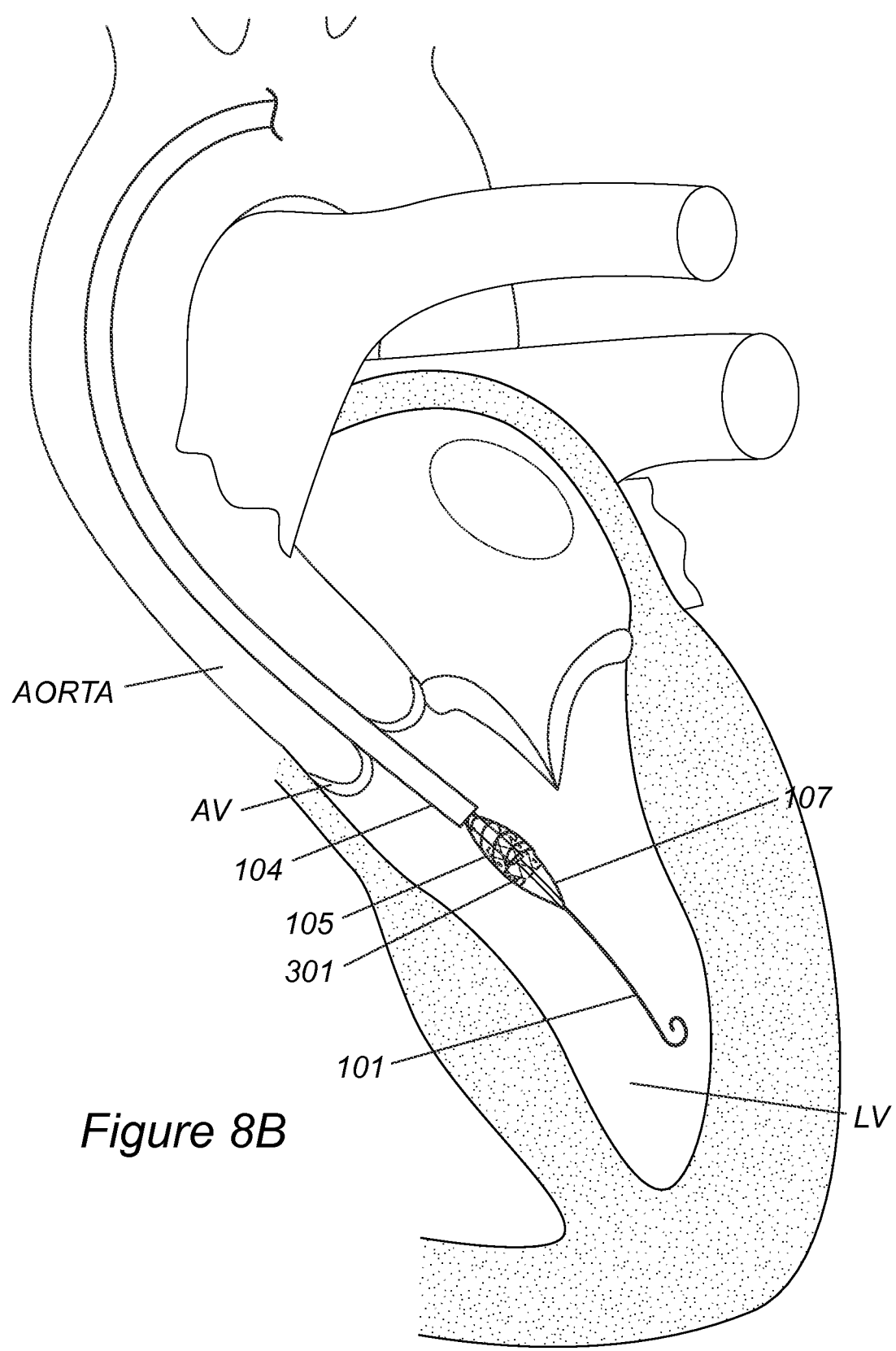
In FIG. 8B, the control wire 106 is pulled to crush the crushing basket 105, the capturing umbrella 107, and the embolized or malpositioned valve 301. The compressed crushing basket 105, capturing umbrella 107, and embolized or malpositioned valve (the crushed objects) are retrieved out of the patient through the second delivery catheter 104. Alternatively, the compressed crushing basket 105, capturing umbrella 107, and embolized or malpositioned valve (the crushed objects) are enclosed into the second delivery catheter 104, and retrieved together with the second delivery catheter 104 out of the patient. In some embodiments the crushed objects are not removed from the body but retracted to a safer location such as but not limited to the descending aorta.

FIG. 8B, the control wire 106 is pulled to crush the crushing basket 105, the capturing umbrella 107, and the embolized or malpositioned valve 301. The compressed crushing basket 105, capturing umbrella 105, and embolized or malpositioned valve (the crushed objects) are retrieved out of the patient, either by retracting the whole system through a sheath, or through the second delivery catheter 104. In this embodiment, as the control wire 106 is retracted and the spiral 109 is slowly contracted crushing the valve. In some embodiments, the connection between the crushing basket 105 and the umbrella 107 will also cause the umbrella 107 to collapse on the valve. In other embodiments, the crushing basket 105 will close and compress over both the valve and the umbrella 105. Alternatively, the compressed crushing basket 105, capturing umbrella 107, and embolized or malpositioned valve (the crushed objects) are enclosed into the second delivery catheter 104, and retrieved together with the second delivery catheter 104 out of the patient. In some embodiments the crushed objects are not removed from the body but retracted to a safer location such as but not limited to the descending aorta.

Figure 9A:
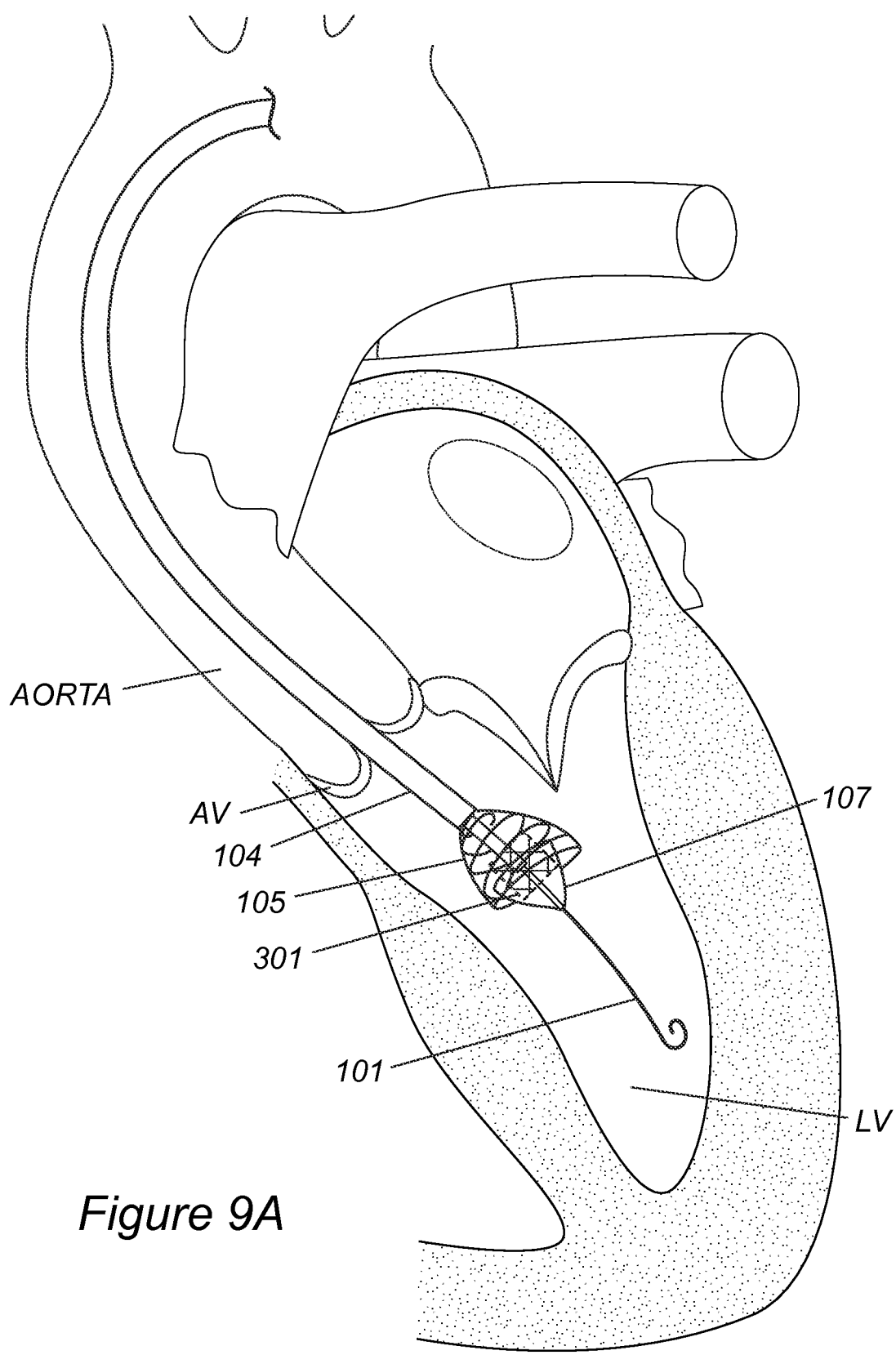
FIG. 9A depicts in accordance with various embodiments of the present invention, a cross sectional view of the expanded crushing basket 105 engulfing the capturing umbrella 107 and the embolized or malpositioned valve 301. The expanded crushing basket 105 is configured in sufficient size to accommodate the expanded capturing umbrella 107 together with the captured valve 301.
Figure 9B:
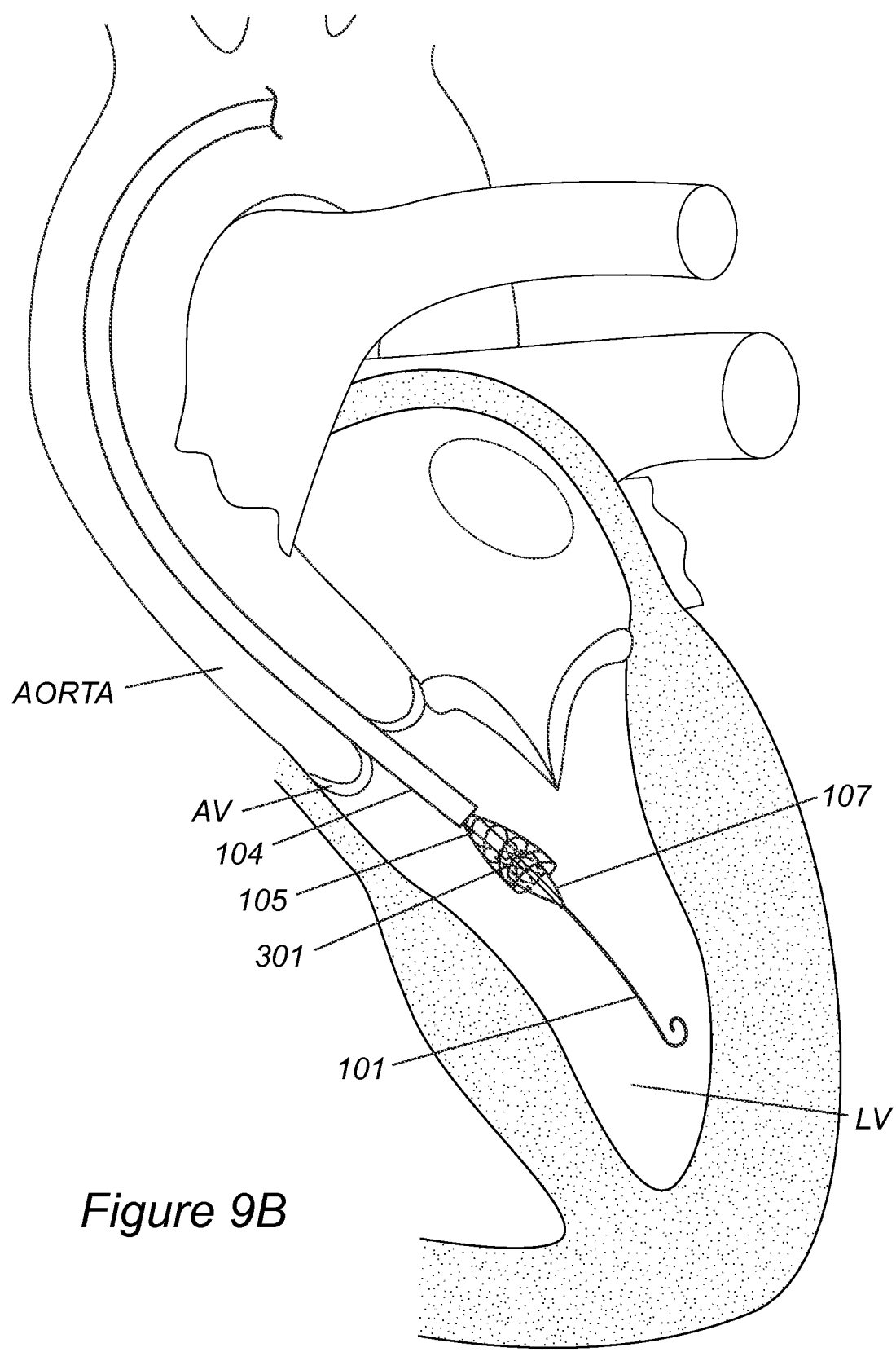
In FIG. 9B, the control wire 106 is pulled to crush the crushing basket 105, the capturing umbrella 107, and the embolized or malpositioned valve. The compressed crushing basket 105, capturing umbrella 107, and embolized or malpositioned valve (the crushed objects) may be retrieved out of the patient through the second delivery catheter 104. Alternatively, the compressed crushing basket 105, capturing umbrella 107, and embolized or malpositioned valve (the crushed objects) are refracted either close to or into the second delivery catheter 104, and retrieved together with the second delivery catheter 104 out of the patient. In some embodiments the crushed objects are not removed from the body but retracted to a safer location such as but not limited to the descending aorta.

FIG. 9A depicts in accordance with various embodiments of the present invention, a cross sectional view of the expanded crushing basket 105 engulfing the capturing umbrella 107 and the embolized or malpositioned valve 301. The expanded crushing basket 105 is configured to be sufficiently large to accommodate the expanded capturing umbrella 107 together with the captured valve 301. In FIG. 9B, the control wire 106 is pulled to crush the crushing basket 105, the capturing umbrella 107, and the embolized or malpositioned valve. The compressed crushing basket 105, capturing umbrella 107, and embolized or malpositioned valve (the crushed objects) are retrieved out of the patient through the second delivery catheter 104. Alternatively, the compressed crushing basket 105, capturing umbrella 107, and embolized or malpositioned valve (the crushed objects) are enclosed into the second delivery catheter 104, and retrieved together with the second delivery catheter 104 out of the patient. In some embodiments the crushed objects are not removed from the body but retracted to a safer location such as but not limited to the descending aorta.

Figure 10E:
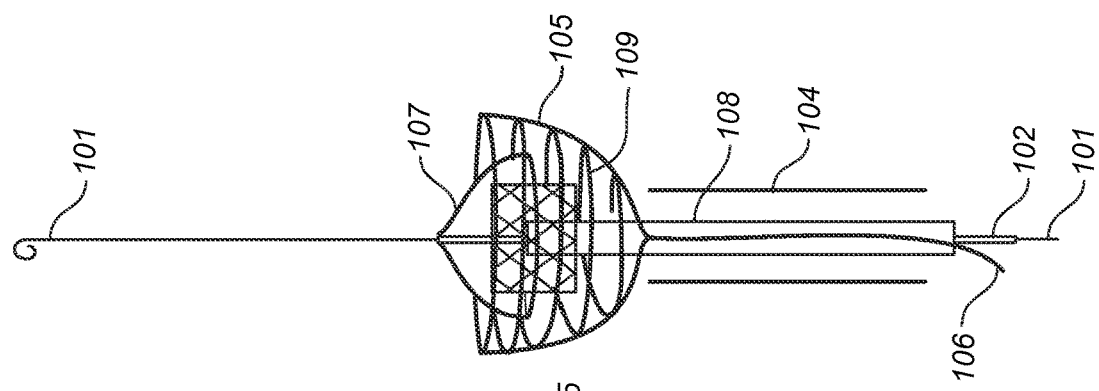
FIGS. 10A-E depict, in accordance with various embodiments of the present invention, cross sectional views of a device for percutaneously retrieving an embolized or malpositioned heart valve or foreign bodies in a patient's heart.
Figure 10D:
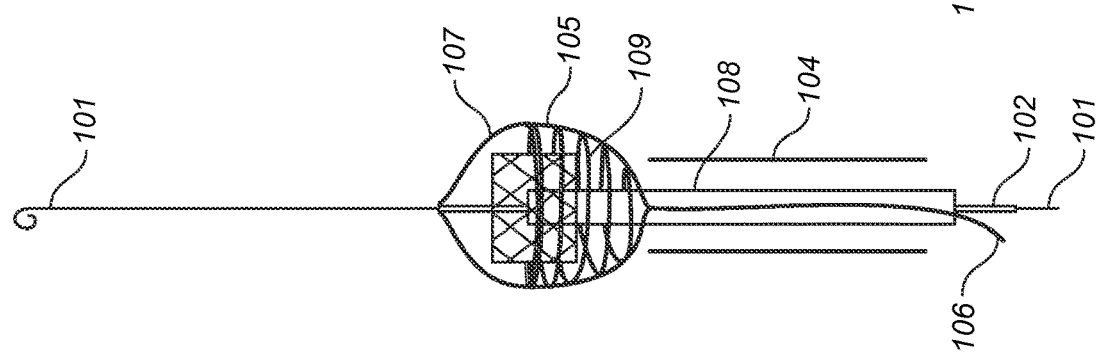
Figure 10C:
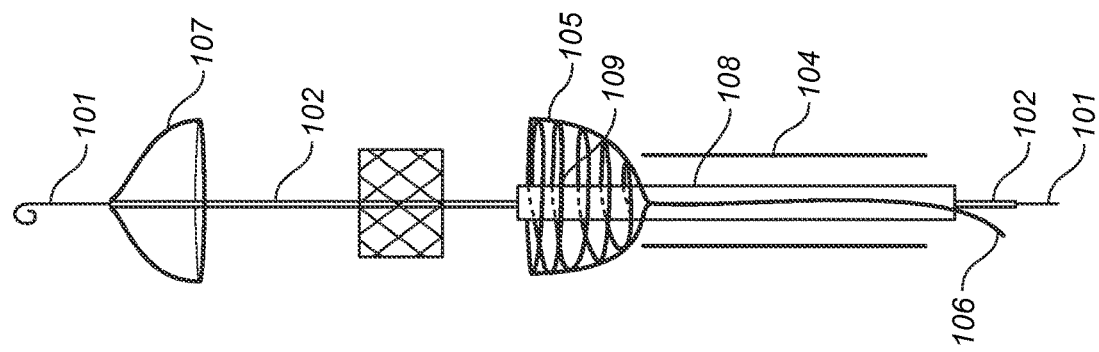
Figure 10B:
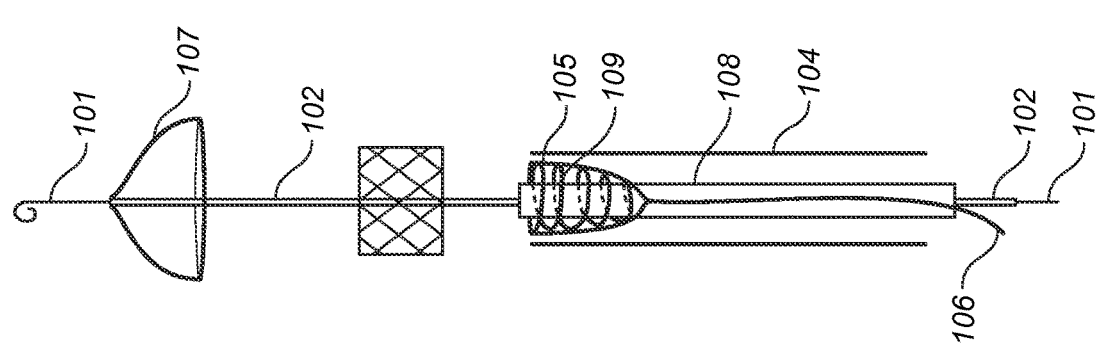
Figure 10A:
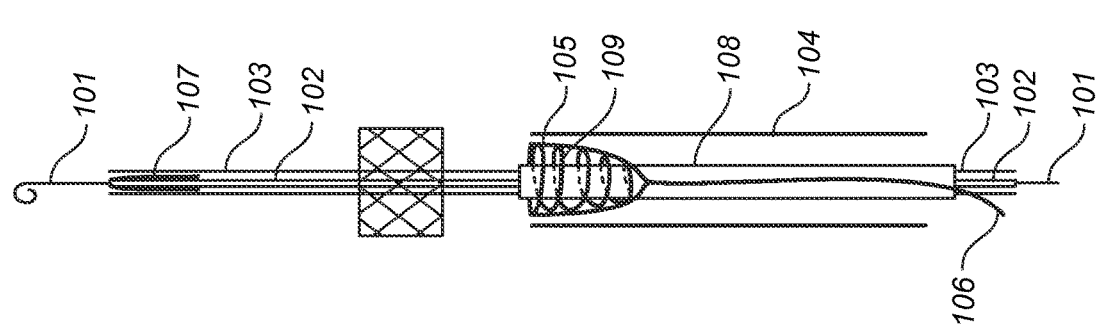

FIGS. 10A-E depict, in accordance with various embodiments of the present invention, cross sectional views of a device for percutaneously retrieving an embolized or malpositioned heart valve or foreign bodies in a patient's heart. In this embodiment, instead of separately sending in the first component, completely retracting the first delivery catheter 103, and then sending in a second component, the first and second components may be sent in together, with the first component protruding out from the second component. In FIG. 10A, the first component (including 102, 103 and 107) is inserted into the second component (including 104, 105, 106, and 108). For example, the second hollow shaft 108 may fit over the first delivery catheter 104. A guide wire 101 is in place and the leading end of the first hollow shaft 102 can be advanced over the trailing end of the guide wire 101; a capturing umbrella 107 is mounted at or near the leading end of the first hollow shaft 102; and when a first delivery catheter 103 encloses the capturing umbrella 107, the capturing umbrella 107 is compressed. The first delivery catheter is inserted into a second hollow shaft 108; a crushing basket 105 is mounted at or near the leading end of the second hollow shaft 108; and when a second delivery catheter 104 encloses the crushing basket 105, the crush basket 105 is compressed. The first component protrudes outside the second component so that the capturing umbrella 107 is located distal to the crushing basket 105. The device is guided over the guide wire 101. Then, the device including the first component that protrudes out through from the second component may be advanced so that the first delivery catheter 104 and other elements of the first component may be inserted through the lumen of the embolized or malpositioned valve. The caregiver would stop inserting it through when the embolized or malpositioned valve is located between the capturing umbrella 107 and the crushing basket 105. In FIG. 10B, when the first delivery catheter 103 is retracted, the capture umbrella 107 expands. In FIG. 10C, when the second delivery catheter 104 is retracted, the crushing basket 105 is expanded. In some embodiments, the crushing basket 105 includes a spiral 109 that may be utilized to crush the valve and other components. A control wire 106 is connected to the spiral 109 and threaded through the second hollow shaft 108. When the control wire 106 is pulled, the crushing basket 105 is compressed to crush the crushing basket 105 and objects engulfed in the crushing basket 105. In FIG. 10D, in some embodiments, the expanded crushing basket 105 and the expanded capturing umbrella 107 are connected to enclose an embolized or malpositioned valve as disclosed herein. Various connecting means can be used to connect the openings of the expanded crushing basket 105 and the expanded capturing umbrella 107. Three examples of click-and-lock systems are shown in FIG. 8A. The control wire 106 can be pulled to crush the crushing basket 105, the capturing umbrella 107, and the embolized or malpositioned valve. In FIG. 10E, in other embodiments, the expanded crushing basket 105 engulfs the capturing umbrella 107 and an embolized or malpositioned valve. The expanded crushing basket 105 is configured in sufficient size to accommodate the expanded capturing umbrella 107 together with the captured valve. The control wire 106 can be pulled to crush the crushing basket 105, the capturing umbrella, and the embolized or malpositioned valve.

FIGS. 11-14 depict, in accordance with various embodiments of the present invention, cross sectional views of a method for percutaneously retrieving an embolized or malpositioned heart valve in a patient's heart. In this embodiment, the first and second components are advanced down the guidewire 101 at the same time. In other embodiments, the first component may be advanced in position with the umbrella 107 (or crushing basket 105) distal to the valve, and then the second component may be advanced in position with the crushing basket 105 (or umbrella 107) proximal to the valve prior to the retracting of the first delivery catheter 104.

Figure 11:
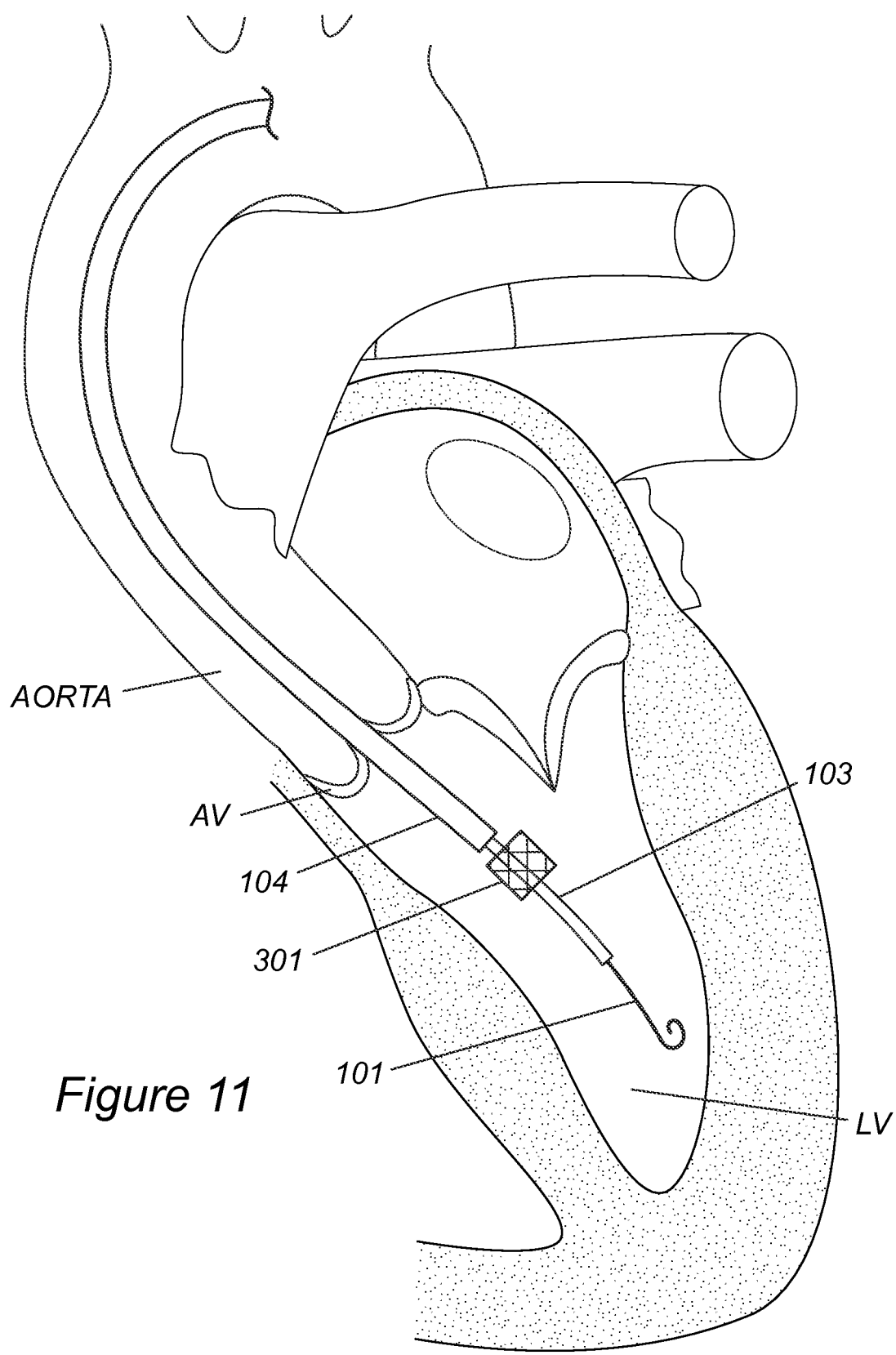
FIGS. 11-14 depict, in accordance with various embodiments of the present invention, cross sectional views of a method for percutaneously retrieving an embolized or malpositioned heart valve in a patient's heart.

FIG. 11 depicts, in accordance with various embodiments of the present invention, cross sectional views of an example where a TAVR device has embolized or malpositioned into the left ventricle. A guide wire 101 is inserted through aorta into a patient's left ventricle, where a heart valve 301 is embolized or malpositioned; the guide wire 101 is advanced through the embolized or malpositioned heart valve 301; the guide wire 101 may, as is more frequently the case, already be in place through the embolized or malpositioned heart valve as transcatheter heart valves are implanted over a guide wire 101; the leading end of the first hollow shaft 102 is advanced over the trailing end of a guide wire 101 until the capturing umbrella 107 passes the embolized or malpositioned valve and until the crushing basket 105 enters the patient's left ventricle but does not pass the embolized or malpositioned valve. As a result, the embolized or malpositioned valve is located between the crushing basket 105 and the capturing umbrella 107 i.e. on the ventricular (proximal) aspect of the crushing basket and on the aortic (distal) aspect of the capturing umbrella.

Figure 12:
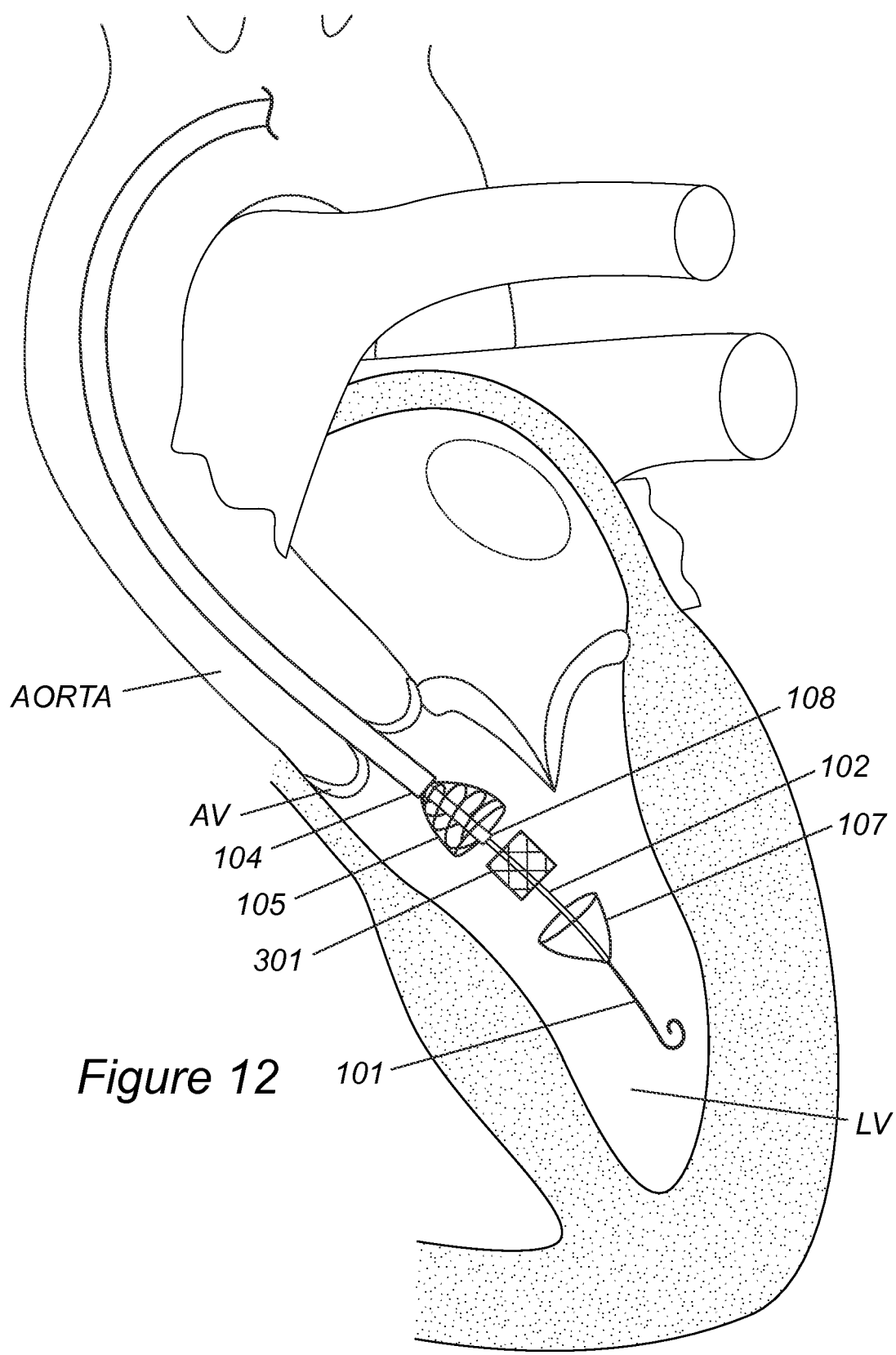

FIG. 12 depicts, in accordance with various embodiments of the present invention, a cross sectional view of the first delivery catheter 103 completely retracted to expand the capturing umbrella 107, and the second delivery catheter 104 is partially retracted to expand the crushing basket 105.

Figure 13:
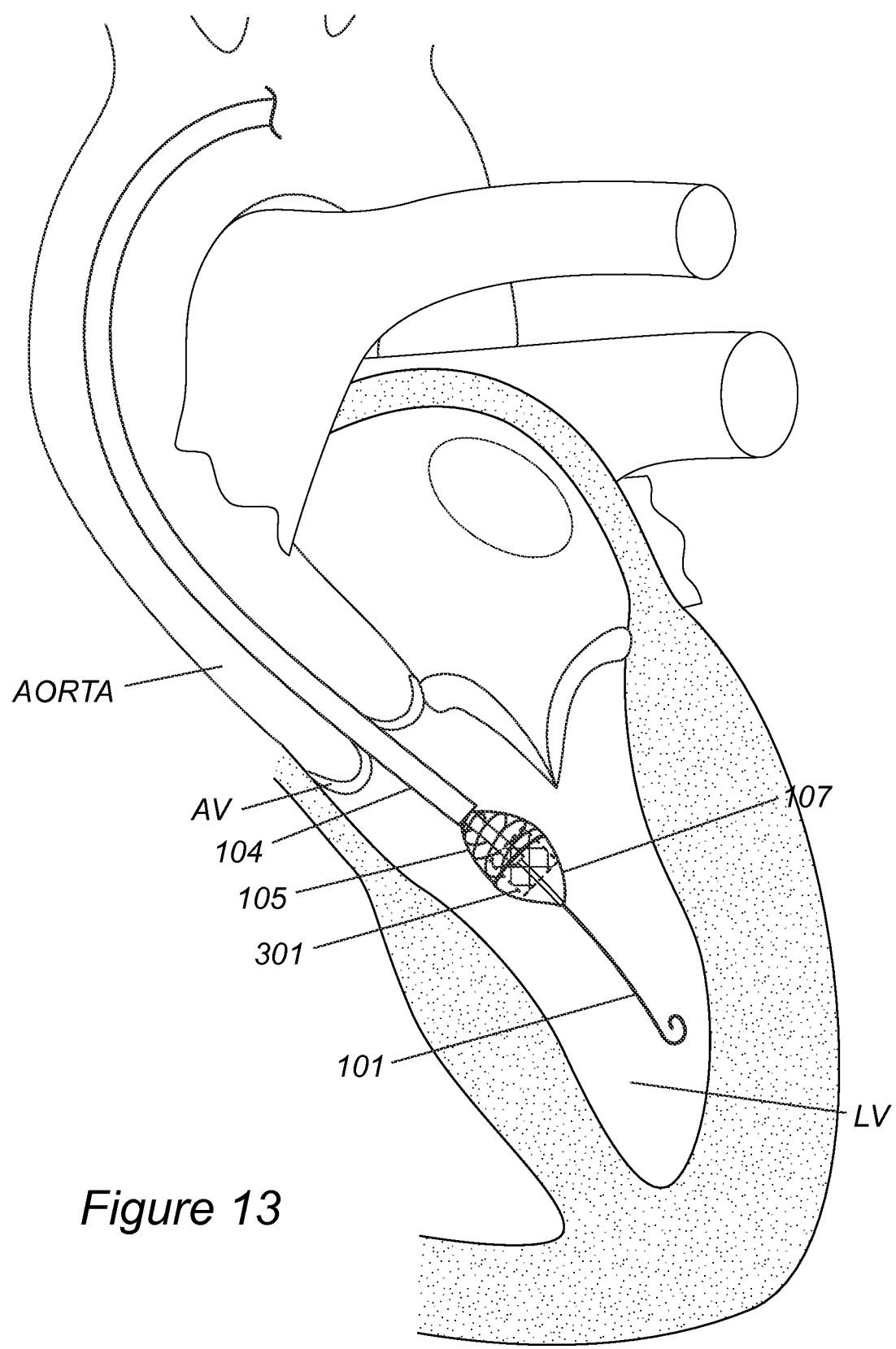

FIG. 13 depicts, in accordance with various embodiments of the present invention, a cross sectional view of, the expanded crushing basket 105 and the expanded capturing umbrella 107 connected to enclose an embolized or malpositioned valve. Various connecting means can be used to connect the openings of the expanded crushing basket 105 and the expanded capturing umbrella 107. Three examples of click-and-lock systems are shown in FIG. 8A.

Figure 14:
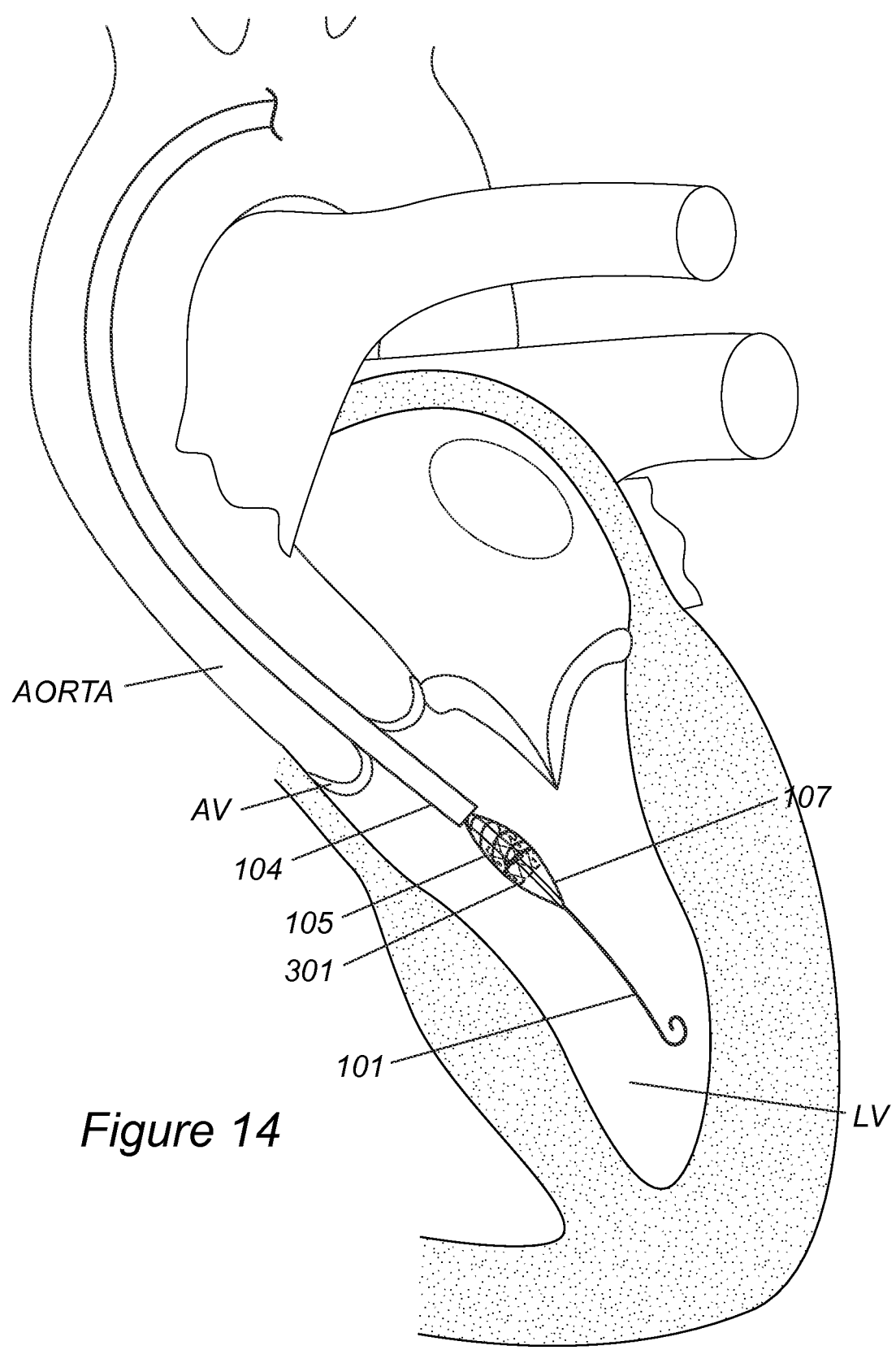

FIG. 14 depicts, in accordance with various embodiments of the present invention, a cross sectional view of, the control wire 106 pulled to crush the crushing basket 105, the capturing umbrella 107, and the embolized or malpositioned valve 301. The compressed crushing basket, capturing umbrella, and embolized or malpositioned valve (the crushed objects) are retrieved out of the patient through the second delivery catheter 104. Alternatively, the compressed crushing basket, capturing umbrella, and embolized or malpositioned valve (the crushed objects) are enclosed into or close to the second delivery catheter 104, and retrieved together with the second delivery catheter out of the patient. In some embodiments the crushed objects are not removed from the body but retracted to a safer location such as but not limited to the descending aorta.

Figures 15A, 15B, 15C, 15D, 15E:
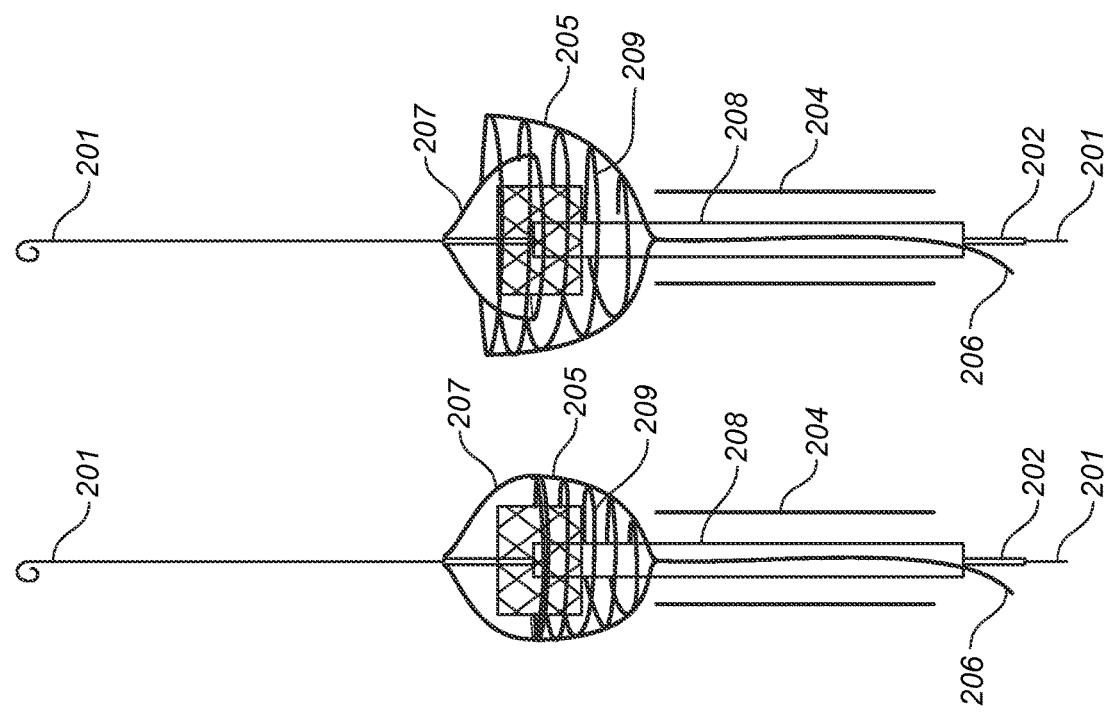
FIGS. 15A-E depict, in accordance with various embodiments of the present invention, cross sectional views of a device for percutaneously retrieving an embolized or malpositioned heart valve or foreign bodies in a patient's heart.

FIGS. 15A-E depict, in accordance with various embodiments of the present invention, cross sectional views of a device for percutaneously retrieving an embolized or malpositioned heart valve or foreign bodies in a patient's heart. In this embodiment, the first component and second components are advanced together so that the distal ends of the first and second component are relatively flush. In some embodiments, using this configuration allows the designer to not utilize a first delivery catheter 104 because the lumen of the second hollow tube 208 may be large enough to fit over and restrain the umbrella 207 until the second hollow tube 208 is retracted to open the umbrella 207. In FIG. 15A, a guide wire 201 is inserted into a first hollow shaft 202. A capturing umbrella 207 is mounted at or near the leading end of the first hollow shaft 202. A second hollow shaft 208 encloses the first hollow shaft 202 and the compressed capturing umbrella 207. A crushing basket 205 is mounted at or near the leading end of the second hollow shaft 208. A delivery catheter 204 encloses the second hollow shaft 208 and the compressed crushing basket 205. The crushing basket 205 comprises a spiral 209. A control wire 206 is connected to the spiral 209 and threaded through the second hollow shaft 208. When the control wire 206 is pulled, the crushing basket 205 is compressed to crush the crushing basket 205 and objects engulfed in the crushing basket 205. The device is guided over the guide wire 101 through an embolized or malpositioned valve to be retrieved.

In FIG. 15B, when the second hollow shaft 208 is retracted, the first hollow shaft 202 is exposed and the capture umbrella 207 is expanded. In FIG. 15C, when the delivery catheter 204 is retracted, the crushing basket 205 is expanded. In FIG. 15D, in some embodiments, the expanded crushing basket 205 and the expanded capturing umbrella 207 are connected to enclose an embolized or malpositioned valve. Various connecting means can be used to connect the openings of the expanded crushing basket 205 and the expanded capturing umbrella 207. Three examples of click-and-lock systems are shown in FIG. 8A. The control wire 206 can be pulled to crush the crushing basket 205, the capturing umbrella 207, and the embolized or malpositioned valve. In FIG. 15E, in other embodiments, the expanded crushing basket 205 engulfs the capturing umbrella 207 and an embolized or malpositioned valve. The expanded crushing basket 205 is configured in sufficient size to accommodate the expanded capturing umbrella 207 together with the captured valve. The control wire 206 can be pulled to crush the crushing basket, the capturing umbrella, and the embolized or malpositioned valve.

In accordance with the present invention, one of ordinary skill in the art would readily recognize that the dimensions, sizes, lengths, diameters, heights, widths, and thickness of various components of the device described herein could be appropriately configured based on many factors, including but not limited to, the object to be retrieved, the anatomical location, and the surgical procedure. For example, the device as a whole can be configured with appropriate dimensions to be inserted into the left ventricle, right ventricle, left atrium, right atrium, ascending aorta, superior vena cava, or inferior vena cava.

In accordance with the present invention, as transcatheter surgeries are a known procedure, one of ordinary skill in the art would readily recognize that the methods provided herein could involve other additional steps, which are not described in details. These additional steps include, but are not limited to, anesthesia, sterilization, heparinization, accessing the patient's heart via various routes such as femoral, transaortic and transapical approaches, ventricular pacing, stitching and percutaneous vascular closure.

In accordance with the present invention, the device and method described herein are not limited to a percutaneous approach. One of ordinary skill in the art would readily recognize that various directional approaches to an embolized or malpositioned valve can be used. In some embodiments, the approach is through blood vessels, for example, from femoral artery or sublavian or axillary or carotid arteries to the ascending aorta to the left ventricle. In other embodiments, the approach is more direct, for example, from the ascending aorta to the left ventricle. In still other embodiments, the approach is transapical, that is, to access a patient's heart chamber through the heart apex and to use the devices described here to transapically retrieve an embolized or malpositioned heart valve.

Still in accordance with the present invention, the devices and methods described herein are useful for retrieving a blood emboli or foreign bodies in a patient's heart chamber. One principle for using the devices described herein to retrieve an object of interest is: place the capturing umbrella beyond (distal to) the object, place the crushing basket behind (proximal to) the object, expand the capturing umbrella and the crushing basket to their full dimensions, move the expanded capturing umbrella and crushing basket toward each other to capture the object in between, and pull the control wire to crush the captured objected for retrieval.

EXAMPLES

Example 1

Surgical Procedure

After induction of anesthesia and sterile preparation, a temporary transvenous pacing wire is inserted into the right ventricle via the femoral vein. Percutaneous femoral access is performed including a pre-closure technique using two orthogonal Proglide technologies is performed and a wire is inserted through the same puncture site in standard fashion. A sheath for the TAVR procedure, a sheath with internal dimension 14-24 Fr, is inserted over the wire. The subject is heparinized with an activated clotting time (ACT) over 250 sec. The aortic valve is crossed retrogradely and a stiff guide wire is inserted into the left ventricle in standard fashion. The transcatheter valve is advanced over the guide wire and correct placement and implantation is attempted with rapid right ventricular pacing but results in heart valve embolization into the left ventricle.

The stiff guide wire 101 is still positioned through the embolized or malpositioned heart valve (FIG. 2). The first component as shown in FIG. 1A is advanced over the guide wire 101 into the left ventricle until its leading end passes the embolized or malpositioned valve so that the capturing umbrella 105 is located beyond (distal to) the embolized or malpositioned valve (FIG. 3A and FIG. 3B). The first delivery catheter 103 of the first component is completely retracted to expand the capturing umbrella 105 distal to the embolized or malpositioned valve (FIG. 4). Next, the expanded capturing umbrella 105 is pulled back to capture and stabilize the embolized or malpositioned valve (FIG. 5). The second component as shown in FIG. 1C is advanced over the first hollow shaft 102 of the first component, until the crushing basket 105 enters the patient's left ventricle but does not pass the embolized or malpositioned valve (FIG. 6A and FIG. 6B). The second delivery catheter 104 is partially retracted to expand the crushing basket 105 proximal to the embolized or malpositioned valve (FIG. 7).

In some embodiments, the expanded crushing basket 105 and the expanded capturing umbrella 107 are moved toward each other and connected. As a result, the embolized or malpositioned valve is enclosed by the expanded crushing basket 105 and the expanded capturing umbrella 107 (FIG. 8A). Various connecting means can be used to connect the openings of the expanded crushing basket 105 and the expanded capturing umbrella 107. Three examples of click-and-lock systems are shown here on the right. Next, the control wire 106 is pulled to crush the crushing basket 105, the capturing umbrella 107, and the embolized or malpositioned valve (FIG. 8B). Following this, the crushed objects (the compressed crushing basket, capturing umbrella, and embolized or malpositioned valve) are retrieved out of the patient through the second delivery catheter 104. Alternatively, the crushed objects are enclosed into the second delivery catheter 104, and retrieved together with the second delivery catheter 104 out of the patient. In some embodiments the crushed objects are not removed from the body but retracted to a safer location such as but not limited to the descending aorta.

In other embodiments, the expanded crushing basket 105 is used to engulf the capturing umbrella 107 and the embolized or malpositioned valve. The expanded crushing basket 105 is configured in sufficient size to accommodate the expanded capturing umbrella 107 together with the captured valve. As a result, the embolized or malpositioned valve is enclosed by the expanded crushing basket 105 and the expanded capturing umbrella 107 (FIG. 9A). Next, the control wire 106 is pulled to crush the crushing basket 105, the capturing umbrella 107, and the embolized or malpositioned valve (FIG. 9B). Following this, the crushed objects (compressed crushing basket, capturing umbrella, and embolized or malpositioned valve) are retrieved out of the patient through the second delivery catheter 104. Alternatively, the crushed objects are enclosed into the second delivery catheter 104, and retrieved together with the second delivery catheter 104 out of the patient. In some embodiments the crushed objects are not removed from the body but retracted to a safer location such as but not limited to the descending aorta.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A device, comprising:
a guide wire;
a first component, comprising:
a first hollow shaft with a first leading end and a first trailing end, wherein the leading end of the first hollow shaft is configured so that it may be advanced over the first trailing end of the guide wire;
a capturing umbrella mounted on the first hollow shaft near or at the first leading end, wherein the capturing umbrella has a compressed form and an expanded form; and
a first delivery catheter housing the first hollow shaft and the capturing umbrella, wherein the capturing umbrella is compressed when the first delivery catheter encloses the capturing umbrella, and wherein the capturing umbrella is expanded when the first delivery catheter does not enclose the capturing umbrella; a second component, comprising:
a second hollow shaft with a second leading end and a second trailing end, wherein the first hollow shaft can be inserted into the second hollow shaft;
a crushing basket comprising a frame mounted on the second hollow shaft near or at the second leading end, wherein the crushing basket has a compressed form and an expanded form and a spiral wire looped through the frame;
a second delivery catheter housing the second hollow shaft and the crushing basket, wherein the crushing basket is compressed when the second delivery catheter encloses the crushing basket, and wherein the crushing basket is expanded when the second delivery catheter does not enclose the crushing basket; and
a control wire, wherein the control wire is connected to the spiral wire and is threaded through the second hollow shaft, wherein the frame of the crushing basket is compressed when the control wire is pulled which pulls on the spiral wire and moves the spiral wire relative to the frame and reduces the size of the spiral wire and frame, and wherein the crushing basket is expanded when the control wire is not pulled; and
wherein an opening of the expanded capturing umbrella and an opening of the expanded crushing basket face each other.

2. The device of claim 1, wherein the capturing umbrella comprises a frame made of nitinol, iron, platinum, titanium, nickel, chromium, cobalt, stainless steel, nickel-chromium, or cobalt-chromium, or a combination thereof.

3. The device of claim 1, wherein the capturing umbrella comprises a mesh made of nitinol, iron, platinum, titanium, nickel, chromium, cobalt, stainless steel, nickel-chromium, or cobalt-chromium, or a combination thereof.

4. The device of claim 1, wherein the spiral is comprised of nitinol, iron, platinum, titanium, nickel, chromium, cobalt, stainless steel, nickel-chromium, or cobalt-chromium, or a combination thereof.

5. The device of claim 1, wherein the control wire is made of nitinol, iron, platinum, titanium, nickel, chromium, cobalt, stainless steel, nickel-chromium, or cobalt-chromium, or a combination thereof.

6. The device of claim 1, wherein the expanded crushing basket has an expanded radius that is large enough to engulf the expanded capturing umbrella.

7. A method, comprising:
providing the device of claim 1;
using the guide wire already in place or inserting the guide wire into a patient's heart chamber, where a heart valve is embolized or malpositioned;
if the wire is not in place, advancing the guide wire through the embolized or malpositioned heart valve;
advancing the first component over the guide wire until the capturing umbrella passes the embolized or malpositioned valve;
retracting the first delivery catheter to expand the capturing umbrella; advancing the second component over the first hollow shaft until the crushing basket enters the patient's heart chamber but does not pass the embolized or malpositioned valve;
retracting the second delivery catheter to expand the crushing basket; using the expanded crushing basket to engulf the capturing umbrella and the embolized or malpositioned valve; and
pulling the control wire to compress the crushing basket, the capturing umbrella, and the embolized or malpositioned valve.

8. The method of claim 7, further comprising retrieving the compressed crushing basket, capturing umbrella, and embolized or malpositioned valve out of the patient through the second delivery catheter.

9. The method of claim 7, further comprising:
enclosing the compressed crushing basket, capturing umbrella, and embolized or malpositioned valve into the second delivery catheter; and
retrieving the second delivery catheter together with the compressed crushing basket, capturing umbrella, and embolized or malpositioned valve out of the patient.

10. The device of claim 1, further comprising a connecting means for connecting the openings of the expanded capturing umbrella and the expanded crushing basket.

11. The device of claim 10, wherein the capturing umbrella and the crushing basket are compressed when their openings are connected and the control wire is pulled.

12. A method, comprising:
providing the device of claim 10;
if the wire is not already present, inserting the guide wire into a patient's heart chamber, where a heart valve is embolized or malpositioned;
if the wire is not already present, advancing the guide wire through the embolized or malpositioned heart valve;
advancing the first component over the guide wire until the capturing umbrella passes the embolized or malpositioned valve;
retracting the first delivery catheter to expand the capturing umbrella;
advancing the second component over the first hollow shaft until the crushing basket enters the patient's heart chamber but does not pass the embolized or malpositioned valve;
retracting the second delivery catheter to expand the crushing basket; connecting the expanded crushing basket and the expanded capturing umbrella to enclose the embolized or malpositioned valve; and
pulling the control wire to compress the crushing basket, the capturing umbrella, and the embolized or malpositioned valve.

13. The method of claim 12, further comprising retrieving the compressed crushing basket, capturing umbrella, and embolized or malpositioned valve out of the patient through the second delivery catheter.

14. The method of claim 12, further comprising:
enclosing the compressed crushing basket, capturing umbrella, and embolized or malpositioned valve into the second delivery catheter; and
retrieving the second delivery catheter together with the compressed crushing basket, capturing umbrella, and embolized or malpositioned valve out of the patient.

15. A device, comprising:
a guide wire;
a first component, comprising:
a first hollow shaft with a first leading end and a first trailing end, wherein the leading end of the first hollow shaft is configured so that it can be advanced over the first trailing end of a guide wire;
a capturing umbrella mounted on the first hollow shaft near or at the first leading end, wherein the capturing umbrella has a compressed form and an expanded form; and
a first delivery catheter housing the first hollow shaft and the capturing umbrella, wherein the capturing umbrella is compressed when the first delivery catheter encloses the capturing umbrella, and wherein the capturing umbrella is expanded when the first delivery catheter does not enclose the capturing umbrella;
a second component, comprising:
a second hollow shaft with a second leading end and a second trailing end,
wherein the first component can be inserted in the second hollow shaft;
a crushing basket comprising a frame mounted on the second hollow shaft near or at the second leading end, wherein the crushing basket has a compressed form and an expanded form and a spiral looped through the frame;
a second delivery catheter housing the second hollow shaft and the crushing basket, wherein the second delivery catheter is configured so that the crushing basket is compressed when the second delivery catheter encloses the crushing basket, and wherein the second delivery catheter is configured so that the crushing basket is expanded when the second delivery catheter does not enclose the crushing basket; and
a control wire, wherein the control wire is connected to the spiral and is threaded through the second hollow shaft, wherein the spiral is only threaded through a distal end of the crushing basket so that it is compressed when the control wire is pulled which pulls on the spiral and reduces the size of the spiral and only the distal end of the crushing basket, and wherein the distal end of the crushing basket is expanded when the control wire is not pulled;
a second control wire, wherein the second control wire is connected to a second spiral and threaded through the second hollow shaft, wherein an entirety of the crushing basket is compressed when the second control wire is pulled which pulls on the second spiral and reduces the size of the second spiral and the crushing basket; and
wherein an opening of the expanded capturing umbrella and an opening of the expanded crushing basket face each other.

16. The device of claim 15, wherein the expanded crushing basket can engulf the expanded capturing umbrella, and wherein the capturing umbrella and the crushing basket are compressed when the control wire is pulled.

17. A method, comprising:
providing the device of claim 15;
inserting the guide wire into a patient's heart chamber, where a heart valve is embolized or malpositioned;
advancing the guide wire through the embolized or malpositioned heart valve; advancing the first component over the guide wire until the capturing umbrella passes the embolized or malpositioned valve;
advancing the second component over the first component until the crushing basket enters the patient's heart chamber but does not pass the embolized or malpositioned valve;
retracting the first delivery catheter to expand the capturing umbrella; retracting the second delivery catheter to expand the crushing basket; using the expanded crushing basket to engulf the capturing umbrella and the embolized or malpositioned valve; and
pulling the control wire to compress the crushing basket, the capturing umbrella, and the embolized or malpositioned valve.

18. The device of claim 15, further comprising a connecting means for connecting the openings of the expanded capturing umbrella and the expanded crushing basket.

19. The device of claim 18, wherein the capturing umbrella and the crushing basket are compressed when their openings are connected and the control wire is pulled.

20. A method, comprising:
providing the device of claim 18;

inserting the guide wire into a patient's heart chamber, where a heart valve is embolized or malpositioned;

advancing the guide wire through the embolized or malpositioned heart valve; advancing the first component over the guide wire until the capturing umbrella is distal to the embolized or malpositioned valve;

advancing the second component over the first component until the crushing basket enters the patient's heart chamber but does not pass the embolized or malpositioned valve;

retracting the first delivery catheter to expand the capturing umbrella; retracting the second delivery catheter to expand the crushing basket; connecting the expanded crushing basket and the expanded capturing umbrella to enclose the embolized or malpositioned valve; and pulling the control wire to compress the crushing basket, the capturing umbrella, and the embolized or malpositioned valve.

21. A device, comprising:

a guide wire;

a first hollow shaft with a first leading end and a first trailing end, wherein the first hollow shaft is configured so that the guide wire can be inserted into the first hollow shaft;

a capturing umbrella mounted on the first hollow shaft near or at the first leading end, wherein the capturing umbrella has a compressed form and an expanded form;

a second hollow shaft with a second leading end and a second trailing end, the second hollow shaft houses the first hollow shaft and the capturing umbrella, wherein the capturing umbrella is compressed when the second hollow shaft encloses the capturing umbrella, and wherein the capturing umbrella is expanded when the second hollow shaft does not enclose the capturing umbrella;

a crushing basket comprising a frame mounted on the second hollow shaft near or at the second leading end, wherein the crushing basket has a compressed form and an expanded form and a spiral wire looped through the frame;

a delivery catheter housing the second hollow shaft and the crushing basket, wherein the crushing basket is compressed when the delivery catheter encloses the crushing basket, and wherein the crushing basket is expanded when the delivery catheter does not enclose the crushing basket; and a control wire, wherein the control wire is connected to the spiral wire and is threaded through the second hollow shaft, wherein the frame of the crushing basket is compressed when the control wire is pulled which pulls on the spiral wire, which moves the spiral wire relative to the frame and reduces the size of the spiral wire and frame, and wherein the crushing basket is expanded when the control wire is not pulled; and wherein an opening of the expanded capturing umbrella and an opening of the expanded crushing basket face each other.

22. The device of claim 21, wherein the expanded crushing basket is configured so that it is large enough to engulf the expanded capturing umbrella, and wherein the capturing umbrella and the crushing basket are compressed when the control wire is pulled.

23. A method, comprising:

providing the device of claim 21;

if the wire is not in place already, inserting the guide wire into a patient's heart chamber, where a heart valve is embolized or malpositioned;

if the wire is not in place already, advancing the guide wire through the embolized or malpositioned heart valve;

advancing the device over the guide wire, wherein the guide wire is inserted into the first hollow shaft, until the capturing umbrella passes the embolized or malpositioned valve and until the crushing basket enters the patient's heart chamber but remains proximal to the embolized or malpositioned valve; retracting the second hollow shaft to expand the capturing umbrella; retracting the delivery catheter to expand the crushing basket;

using the expanded crushing basket to engulf the capturing umbrella and the embolized or malpositioned valve; and pulling the control wire to compress the crushing basket, the capturing umbrella and the embolized or malpositioned valve.

24. The device of claim 21, further comprising a connecting means for connecting the openings of the expanded capturing umbrella and the expanded crushing basket.

25. The device of claim 24, wherein the capturing umbrella and the crushing basket are compressed when their openings are connected and the control wire is pulled.

26. A method, comprising:

providing the device of claim 24;

if the wire is not in place already, inserting the guide wire into a patient's heart chamber, where a heart valve is embolized or malpositioned;

if the wire is not in place already, advancing the guide wire through the embolized or malpositioned heart valve;

advancing the device over the guide wire, wherein the guide wire is inserted into the first hollow shaft, until the capturing umbrella passes the embolized or malpositioned valve and is distal to the embolized or malpositioned valve, and until the crushing basket enters the patient's heart chamber but does not pass the embolized or malpositioned valve and remains proximal to the embolized or malpositioned valve; retracting the second hollow shaft to expand the capturing umbrella; retracting the delivery catheter to expand the crushing basket;

connecting the expanded crushing basket and the expanded capturing umbrella to enclose the embolized or malpositioned valve; and pulling the control wire to compress the crushing basket, the capturing umbrella and the embolized or malpositioned valve.

* * * * *